(12) United States Patent  
Chachisvilis et al.

(10) Patent No.: US 11,826,130 B2  
(45) Date of Patent: Nov. 28, 2023

(54) SKIN PERFUSION MONITORING DEVICE

(71) Applicant: VeriSkin, Inc., San Diego, CA (US)

(72) Inventors: Mirianas Chachisvilis, San Diego, CA (US); Carl Frederick Edman, San Diego, CA (US); Eugene Tu, San Diego, CA (US)

(73) Assignee: VERISKIN, INC., San Diego, CA (US)

( * ) Notice: Subject to any disclaimer, the term of this patent is extended or adjusted under 35 U.S.C. 154(b) by 72 days.

(21) Appl. No.: 17/379,823

(22) Filed: Jul. 19, 2021

(65) Prior Publication Data

US 2022/0039674 A1 Feb. 10, 2022

Related U.S. Application Data

(63) Continuation of application No. 15/101,604, filed as application No. PCT/US2014/068909 on Dec. 5, 2014, now Pat. No. 11,089,969.

(60) Provisional application No. 61/912,124, filed on Dec. 5, 2013.

(51) Int. Cl.
*A61B 5/026* (2006.01)
*A61B 5/00* (2006.01)
*A61B 8/06* (2006.01)

(52) U.S. Cl.
CPC .......... *A61B 5/0261* (2013.01); *A61B 5/0053* (2013.01); *A61B 5/441* (2013.01); *A61B 5/444* (2013.01); *A61B 5/7282* (2013.01); *A61B 8/06* (2013.01); *A61B 5/6843* (2013.01); *A61B 2562/0233* (2013.01); *A61B 2562/247* (2013.01)

(58) Field of Classification Search
CPC ....... A62B 5/441; A62B 5/444; A62B 5/7282; A61B 2562/0233; A61B 2562/247; A61B 8/06; A61B 8/5223
See application file for complete search history.

(56) References Cited

U.S. PATENT DOCUMENTS

| | | |
|---|---|---|
| 3,698,382 A | 10/1972 | William |
| 4,213,462 A | 7/1980 | Sato |
| 4,538,618 A | 9/1985 | Rosenberg et al. |
| 5,299,570 A | 4/1994 | Hatschek |

(Continued)

FOREIGN PATENT DOCUMENTS

| | | |
|---|---|---|
| WO | WO-2009043028 A2 | 4/2009 |
| WO | WO-2009144623 A1 | 12/2009 |

(Continued)

OTHER PUBLICATIONS

Abraham et al. Dynamics of local pressure-induced cutaneous vasodilation in the human hand. Microvasc Res 61:122-129 (2001).

(Continued)

*Primary Examiner* — Boniface Ngathi  
(74) *Attorney, Agent, or Firm* — Wilson Sonsini Goodrich & Rosati

(57) ABSTRACT

A method and a device for diagnostic of skin cancer and other mammalian skin tissue pathologies are described. The method relies on determination of pathological changes in tissue vascularization and capillary blood flow. The device uses photonic emitters and detectors to characterize temporal and spatial changes in blood flow in response to external perturbation such as external mechanical force or temperature change.

16 Claims, 16 Drawing Sheets

(56) References Cited

U.S. PATENT DOCUMENTS

| | | | |
|---|---|---|---|
| 5,392,777 | A | 2/1995 | Swedlow et al. |
| 5,810,010 | A | 9/1998 | Anbar |
| 5,999,843 | A | 12/1999 | Anbar |
| 6,685,635 | B2 | 2/2004 | Shani et al. |
| 7,184,820 | B2 | 2/2007 | Jersey-Willuhn et al. |
| 8,082,017 | B2 | 12/2011 | Messerges et al. |
| 8,798,704 | B2 | 8/2014 | Mckenna |
| 11,089,969 | B2 * | 8/2021 | Chachisvilis .......... A61B 5/441 |
| 2006/0064024 | A1 | 3/2006 | Schnall |
| 2006/0234383 | A1 | 10/2006 | Gough |
| 2006/0253007 | A1 | 11/2006 | Cheng et al. |
| 2008/0214953 | A1 | 9/2008 | Hashimshony et al. |
| 2009/0143655 | A1 | 6/2009 | Shani |
| 2009/0234206 | A1 | 9/2009 | Gaspard et al. |
| 2009/0306521 | A1 | 12/2009 | Ermakov et al. |
| 2009/0326346 | A1 | 12/2009 | Kracker et al. |
| 2010/0100160 | A1 | 4/2010 | Edman et al. |
| 2010/0286515 | A1 | 11/2010 | Gravenstein et al. |
| 2011/0313235 | A1 | 12/2011 | Gleim |
| 2012/0184831 | A1 | 7/2012 | Seetamraju et al. |
| 2013/0123648 | A1 | 5/2013 | Stampoulidis et al. |
| 2013/0211216 | A9 | 8/2013 | Bezzerides et al. |
| 2013/0253335 | A1 | 9/2013 | Noto et al. |
| 2014/0107493 | A1 | 4/2014 | Yuen et al. |
| 2014/0288386 | A1 | 9/2014 | Zand et al. |
| 2016/0007907 | A1 | 1/2016 | Lancaster et al. |
| 2016/0310023 | A1 | 10/2016 | Chachisvilis et al. |
| 2018/0103873 | A1 * | 4/2018 | Jacquet-Lagreze .......................... A61B 5/02007 |
| 2018/0146866 | A1 | 5/2018 | Chachisvilis et al. |

FOREIGN PATENT DOCUMENTS

| | | |
|---|---|---|
| WO | WO-2009144653 A2 | 12/2009 |
| WO | WO-2012069637 A1 | 5/2012 |
| WO | WO-2015015557 A1 | 2/2015 |
| WO | WO-2015085240 A1 | 6/2015 |
| WO | WO-2016187136 A1 | 11/2016 |

OTHER PUBLICATIONS

Alba-Alejandre et al. Microcirculatory changes in term newborns with suspected infection: an observational prospective study. Int J Ped 2013:768784 (2013).
Baish et al. Fractals and cancer. Cancer Res 60:3683-3688 (2000).
Barnhill et al. Angiogenesis and tumor progression of melanoma. Quantification of vascularity in melanocytic nevi and cutaneous malignant melanoma. Lab Invest 67:331-337 (1992).
Carmeliet et al., Angiogenesis in Cancer and Other Diseases. Nature 407 (2000): 249-257.
Chin et al. Differences in the vascular patterns of basal and squamous cell skin carcinomas explain their differences in clinical behaviour. J Path 200:308-313 (2003).
Cracowski et al. Methodological issues in the assessment of skin microvascular endothelial function in humans. Trends Pharmacol Sci 27:503-508 (2006).
Cugmas et al. Pressure-induced near infrared spectra response as a valuable source of information for soft tissue classification. J Biomed Opt 18(4):047002-1 to 047002-7 (2013).
Dudewicz et al. Entropy-Based Tests of Uniformity. Journal of the American Statistical Association 76:967-974 (1981).
Emmett et al. Angiogenesis and melanoma—from basic science to clinical trials. American J Cancer Res 1:852-868 (2011).
Folkman. Angiogenesis in cancer, vascular, rheumatoid and other disease. Nat Med 1:27-31 (1995).
Fromy et al. Early decrease of skin blood flow in response to locally applied pressure in diabetic subjects. Diabetes 51:1214-1217 (2002).
Garry et al. Cellular mechanisms underlying cutaneous pressure-induced vasodilation: in vivo involvement of potassium channels. Am J Physiol Heart Circ Physiol 289:H174-H180 (2005).
Gaustad et al. Blood supply in melanoma xenografts is governed by the morphology of the supplying arteries. Neoplasia 11:277-285 (2009).
Gessner et al. Mapping microvasculature with acoustic angiography yields quantifiable differences between healthy and tumor-bearing tissue volumes in a rodent model. Radiology 264:733-740 (2012).
Gokce. Clinical assessment of endothelial function: ready for prime time? Circ Cardiovasc Imaging 4:348-350 (2011).
Green et al. Impaired skin blood flow response to environmental heating in chronic heart failure. Eur Heart J 27:338-343 (2006).
Heldin et al. High interstitial fluid pressure—an obstacle in cancer therapy. Nat Rev Cancer 4:806-813 (2004).
Holowatz et al. L-Arginine supplementation or arginase inhibition augments reflex cutaneous vasodilatation in aged human skin. J Physiol 574:573-581 (2006).
Holowatz et al. Local ascorbate administration augments NO- and non-NO-dependent reflex cutaneous vasodilation in hypertensive humans. Am J Physiol Heart Circ Physiol 293:H1090-H1096 (2007).
Holowatz et al. Oral atorvastatin therapy restores cutaneous microvascular function by decreasing arginase activity in hypercholesterolaemic humans. J Physiol 589:2093-2103 (2011).
Holowatz et al. The human cutaneous circulation as a model of generalized microvascular function. J App Phys 105:370-372 (2008).
Israel et al. Peripheral endothelial dysfunction in patients suffering from acute schizophrenia: a potential marker for cardiovascular morbidity? Schizophr Res 128:44-50 (2011).
Jacques. Optical properties of biological tissues: a review. Phys Med Biol 58:R37-61 (2013).
Jain. Determinants of tumor blood flow: a review. Cancer Res 48:2641-2658 (1988).
Kashani-Sabet et al. Tumor vascularity in the prognostic assessment of primary cutaneous melanoma. J Clin Oncol 20:1826-1831 (2002).
Khalil et al. Impaired peripheral endothelial microvascular responsiveness in Alzheimer's disease. Journal of Alzheimer's disease. J Alzheimers Dis 11:25-32 (2007).
Khan et al. Relationship between peripheral and coronary function using laser Doppler imaging and transthoracic echocardiography. Clin Sci (Lond) 115:295-300 (2008).
Kimura et al. Integrated laser Doppler blood flowmeter designed to enable wafer-level packaging. IEEE Trans Biomed Eng 57(8):2026-33 (2010).
Less et al. Geometric resistance and microvascular network architecture of human colorectal carcinoma. Microcirculation 4:25-33 (1997).
Li et al. Initial stages of tumor cell-induced angiogenesis: evaluation via skin window chambers in rodent models. Journal of the National Cancer Institute 92:143-147 (2000).
Livesey et al. Analyzing the distribution of decay constants in pulse-fluorimetry using the maximum entropy method. Biophys J 52:693-706 (1987).
Lo et al. Prediction of Wound Healing Outcome using Skin Perfusion Pressure and Transcutaneous Oximetry: a single-senter experience in 100 patients. Wounds 21:310-316 (2009).
Lunt et al. Interstitial fluid pressure in tumors: therapeutic barrier and biomarker of angiogenesis. Future Oncol 4:793-802 (2008).
Lyng et al. Blood flow in six human melanoma xenograft lines with different growth characteristics. Cancer Res 52:584-592 (1992).
Methods and potential biomarkers for the evaluation of endothelial dysfunction in chronic kidney disease: a critical approach. J Am Soc Hypertens 4:116-127 (2010).
Ming et al. Postoperative relieve of abnormal vasoregulation in carpal tunnel syndrome. Clin Neurol Neurosurg 109:413-417 (2007).
Nishida et al. Angiogenesis in cancer. Vas Health Risk Manag 2:213-219 (2006).
PCT/US2014/068909 International Search Report and Written Opinion dated Apr. 30, 2015.
PCT/US2016/32738 International Search Report and Written Opinion dated Aug. 25, 2016.
Ria et al. Angiogenesis and progression in human melanoma. Dermatol Res Pract 2010:185687 (2010).
Rossi et al. Skin vasodilator function and vasomotion in patients with morbid obesity: effects of gastric bypass surgery. Obes Surg 21:87-94 (2011).

(56) References Cited

OTHER PUBLICATIONS

Rossi et al. The investigation of skin blood flowmotion: a new approach to study the microcirculatory impairment in vascular diseases? Biomed Pharmacother 60:437-442 (2006).
Rousseau et al. Axon-reflex cutaneous vasodilatation is impaired in type 2 diabetic patients receiving chronic low-dose aspirin. Microvasc Res 78:218-223 (2009).
Roustit et al. Abnormal digital neurovascular response to local heating in systemic sclerosis. Rheumatology (Oxford) 47:860-864 (2008).
Sensky et al. Resistance to flow through tissue-isolated transplanted rat tumours located in two different sites. Br J Cancer 67:1337-1341 (1993).
Sevick et al. Geometric resistance to blood flow in solid tumors perfused ex vivo: effects of tumor size and perfusion pressure. Cancer Res 49:3506-3512 (1989).
Simonsen et al. High interstitial fluid pressure is associated with tumor-line specific vascular abnormalities in human melanoma xenografts. PLoS One 7:040006 (2012).
Sokolnicki et al. Contribution of nitric oxide to cutaneous microvascular dilation in individuals with type 2 diabetes mellitus. Am J Physiol Metab 292:E314-E318 (2007).
Spronk et al. Bench-to-bedside review: sepsis is a disease of the microcirculation. Crit Care 8:462-468 (2004).
Srivastava et al. The prognostic significance of tumor vascularity in intermediate-thickness (0.76-4.0 mm thick) skin melanoma. A quantitative histologic study. Am J Pathol 133:419-423 (1988).
Straume et al. Angiogenesis is prognostically important in vertical growth phase melanomas. Int J Oncol 15:595-599 (1999).
Struijker-Boudier et al. Evaluation of the microcirculation in hypertension and cardiovascular disease. Eur Heart J 28:2834-2840 (2007).
Stucker et al. High-resolution laser Doppler perfusion imaging aids in differentiating between benign and malignant melanocytic skin tumours. Acta dermato-vencreologica 82:25-29 (2002).
Thompson-Torgerson et al. Rho kinase-mediated local cold-induced cutaneous vasoconstriction is augmented in aged human skin. Am J Physiol Heart Circ Physiol 293:H30-H36 (2007).
Toth-Jakatics et al. Cutaneous malignant melanoma: correlation between neovascularization and peritumor accumulation of mast cells overexpressing vascular endothelial growth factor. Hum Path 31:955-960 (2000).
Trzepizur et al. Microvascular endothelial function in obstructive sleep apnea: Impact of continuous positive airway pressure and mandibular advancement. Sleep medicine 10:746-752 (2009).
Turner et al. Current concepts in assessment of microvascular endothelial function using laser Doppler imaging and iontophoresis. Trends Cardiovasc Med 18:109-116 (2008).
U.S. Appl. No. 15/101,604 Office Action dated Dec. 22, 2020.
U.S. Appl. No. 15/101,604 Office Action dated May 18, 2020.
U.S. Appl. No. 15/101,604 Office Action dated Sep. 9, 2020.
U.S. Appl. No. 15/574,126 Final Office Action dated Jul. 23, 2021.
U.S. Appl. No. 15/574,126 Office Action dated Oct. 23, 2020.
Velasco et al. Dermatological aspects of angiogenesis. Br J Dermatol 147:841-852 (2002).
Vogt et al. Effects of mechanical indentation on diffuse reflectance spectra, light transmission, and intrinsic optical properties in ex vivo porcine skin. Lasers Surg Med 44(4):303-309 (2012).
Weidner. Intratumor microvessel density as a prognostic factor in cancer. Am J Pathol 147:9-19 (1995).

\* cited by examiner

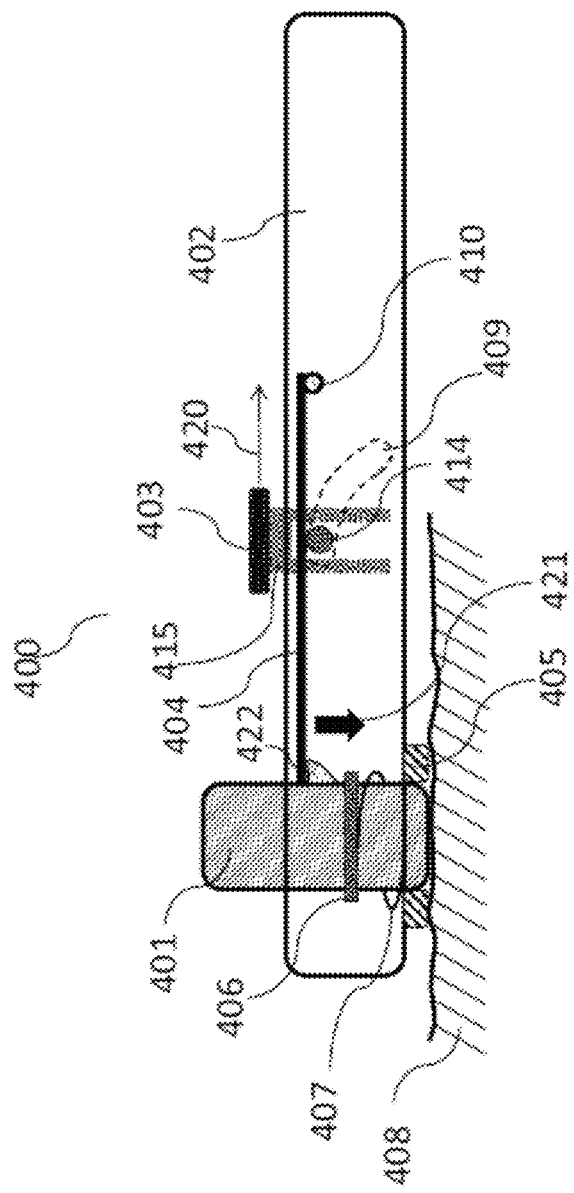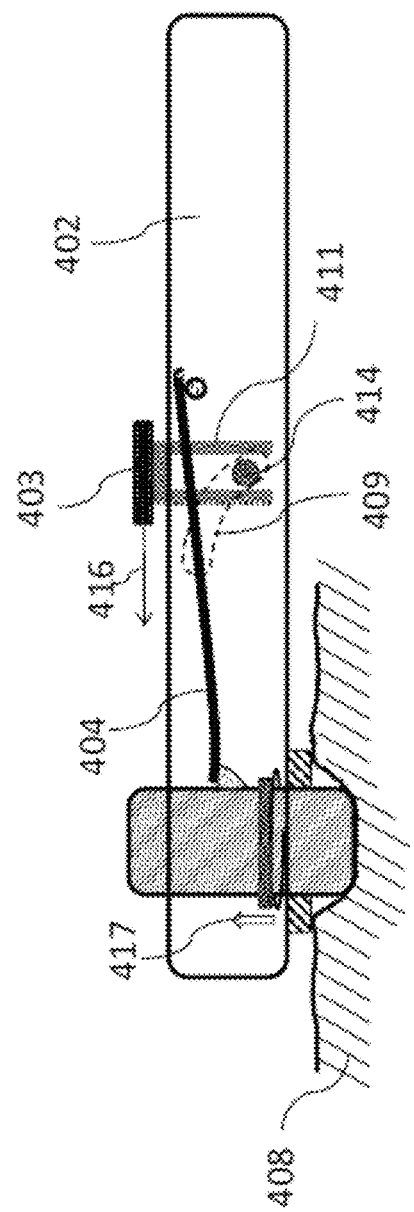
FIG. 4A
FIG. 4B

SKIN PERFUSION MONITORING DEVICE

CROSS-REFERENCE

This application is a continuation of U.S. patent application Ser. No. 15/101,604, filed on Jun. 3, 2016, which is a U.S. National Phase Entry of International Application No. PCT/US2014/068909, filed on Dec. 5, 2014, which claims the benefit of U.S. Provisional Application No. 61/912,124, filed Dec. 5, 2013, each of which is incorporated herein by reference in its entirety.

FIELD OF THE INVENTION

The field of the invention generally relates to the use of an applied force or another external perturbation, such as temperature change in the measurement of cutaneous blood, including dermal capillary, displacement and reperfusion for use in the detection of skin cancer and other mammalian disease states.

BACKGROUND OF THE INVENTION

Assessment of skin capillary blood refill rate has been used for determination of health status, primarily for use as an index of whole body shock or whole body dehydration. Typically, such assessment involves determining the refill time of capillaries located in the skin following the transitory removal of blood via an applied force. Although useful as a general assessment of capillary health and vascular system function, non-invasive devices measuring tissue perfusion parameters have not been shown useful for determining or diagnosing skin disease or other pathological states in subjects.

SUMMARY OF THE INVENTION

The disclosures described herein generally relates to a method and device for the dynamic measurement of skin blood flow parameters (e.g., capillary blood flow parameters) useful in the determination of skin disease states such as skin cancers. An exemplary form of a device comprises an approximately cylindrical inner member and an approximately cylindrical outer member generally arranged about a common axis. Sensors incorporated within the inner member are used, for example, for measurements pertaining to the presence of blood within the region of skin against which the device is positioned, for example, by hand.

In brief, the outer member is configured to form contiguous contact with the skin surface, with the inner member configured to move relative to the outer member. In one embodiment, the device is a hand held device, wherein the outer member is held in contact with the skin surface by a user's hand. Movement of the inner member relative to the outer member allows the inner member upon movement to provide transitory pressure to a portion of the skin surface. This transitory pressure is intended to result in the removal and reperfusion of blood through the skin capillaries so affected by the transitory pressure, which may be monitored by one or more sensors of the device. In one embodiment, the device further comprises one or more sensors that may, in some instances, be contained within the inner member and may, in some instances, be photonic in nature, wherein the one or more sensors are configured for the determination of dynamic blood perfusion parameters within the skin capillary bed during one or more aspects associated with the process of skin blood perfusion associated with the actions of the inner member. In one non-limiting example, the device is configured to be held and positioned on the body by hand.

In a preferred embodiment, the overall shape of the device is that of wand or pen where the outer member also provides a means for being held to the skin surface by a clinician performing the assessment. Other means, such as straps, Velcro, belts or a layer of medical adhesive that immobilize the device with respect to the skin surface, are also readily conceivable. Contained within the device, either in the outer or inner member, depending on the overall configuration, are necessary power sources, e.g., battery, switches, mechanical force actuators or springs to transiently move the inner member, and electronic circuitry and sensors configured for obtaining capillary blood measurements. In certain instances, one or more functions, e.g., data analysis circuitry, power, data display, photonic light sources and sensors, and other components and devices, may be located in a separate portion of the device connected to the inner and outer member portion by means of electrical wires and/or fiber optics.

Data and analysis from the device may be displayed on a small screen located on the outside of the outer aspect of the outer member in a preferred embodiment. In other embodiments, such data may be transmitted either wirelessly or via electrical connection to adjacent data receiving devices for display, storage and further analysis.

Provided herein, in one aspect, is a method to detect a change in blood microcirculation, the method comprising (a) reversibly applying an external force locally to a skin region for a duration of time suitable to alter blood perfusion in the skin region; (b) using one or more photonic excitation sources and one or more detectors to measure one or more blood flow parameters in response to the external force, before, during and/or after application of said external force; (c) analyzing and quantifying the one or more blood flow parameters; and (d) comparing the one or more blood flow parameters to a data set to determine the absence or presence of a disease state. In some embodiments, the one or more photonic excitation sources and one or more detectors to measure one or more blood flow parameters in response to the external force, are used before the application of the external force. In some embodiments, the one or more photonic excitation sources and one or more detectors to measure one or more blood flow parameters in response to the external force, are used during the application of the external force. In some embodiments, the one or more photonic excitation sources and one or more detectors to measure one or more blood flow parameters in response to the external force, are used after the application of the external force. In some embodiments, the one or more photonic excitation sources and one or more detectors to measure one or more blood flow parameters in response to the external force, are used before and during the application of the external force. In some embodiments, the one or more photonic excitation sources and one or more detectors to measure one or more blood flow parameters in response to the external force, are used before and after the application of the external force. In some embodiments, the one or more photonic excitation sources and one or more detectors to measure one or more blood flow parameters in response to the external force, are used during and after the application of the external force. In some embodiments, the one or more photonic excitation sources and one or more detectors to measure one or more blood flow parameters in response to the external force, are used before, during and after the application of the external force. In one embodiment, the data set comprises measured blood flow parameters of at least one skin region in response to an external force, wherein at least one skin region is a reference skin region. A reference skin region includes a skin region having or not having a disease state. In one embodiment, the disease state is cancer. An exemplary cancer is skin cancer. Skin cancer includes stages 0, 1, 2, 3 and 4 of skin cancer. In one embodiment, the method to detect a change in blood microcirculation is performed on both an area of skin of an individual suspected of having a disease, e.g., melanoma, and an area of skin of the same individual which is known to not have the disease, e.g., the reference or control skin region. In another embodiment, a reference region is a region of skin of another individual, wherein the reference region has or does not have a disease state.

Provided herein, in one aspect, is a device for measuring blood microcirculation, the device comprising (a) a means to provide an external force to a skin region, wherein the external force is sufficient in pressure and duration to alter blood perfusion in the skin region; and (b) a sensor comprising a photonic excitation source and a photonic detector, wherein the sensor is configured to measure one or more blood flow parameters prior to, during, and/or after application of an external force to the skin region. In one embodiment, the photonic detector measures an applied photonic energy absorption by a component of blood. In one embodiment, the photonic detector is an imaging detector. In one embodiment, photonic energy is delivered to and collected from one or more areas of the skin region using optical fibers. In one embodiment, photonic energy is delivered to an area of the skin region from the photonic excitation source. In another embodiment, photonic energy is detected from an area of the skin region with the photonic detector. In one embodiment, the sensor comprises a plurality of photonic detectors, wherein each photonic detector is located at a different distance from the photonic excitation source than another photonic detector.

In one aspect, provided herein is a device for measuring blood microcirculation, the device comprising a means to provide an external force to a skin region, wherein the external force is sufficient in pressure and duration to alter blood perfusion in the skin region; and a sensor comprising a photonic excitation source and a photonic detector, wherein the sensor is configured to measure one or more blood flow parameters prior to, during, and/or after application of an external force to the skin region.

The photonic detector measures an applied photonic energy absorption by a component of blood. In one embodiment, the photonic detector is an imaging detector. A photonic energy can be delivered to and collected from one or more areas of the skin region using optical fibers.

In another embodiment, the sensor comprises a plurality of photonic detectors, wherein each receiver for a photonic detector is located at different distances from the emission location of the photonic excitation source of the sensor.

In one aspect, a means to provide an external force to a skin region comprises an inner member configured to move relative to an outer member, allowing for the application of variable pressure to the skin region.

In another aspect, a device is configured to measure one or more blood flow parameters of an area of the skin region, wherein the area is equivalent to or greater than 0.100 mm in diameter.

A device can be configured to measure one or more blood flow parameters of an area of the skin region, wherein the area is between about 1 mm and about 5 mm in diameter.

A device can also be configured to measure one or more blood flow parameters of an area of the skin region, wherein the area is between about 1 mm and about 30 mm in diameter, between about 5 mm and about 30 mm in diameter, between about 5 mm and about 25 mm in diameter, between about 5 mm and about 20 mm in diameter, between about 5 mm and about 15 mm in diameter or between about 5 mm and about 10 mm in diameter, between about 10 mm and about 20 mm in diameter, between about 1 mm and about 10 mm in diameter, between about 1 mm and about 20 mm in diameter or between about 10 mm and about 30 mm in diameter.

A photonic excitation source can emit light at wavelengths below 400 nm, between 400 nm and 450 nm, between 450 nm and 500 nm, between 500 nm and 550 nm, between 550 nm and 600 nm, between 600 nm and 650 nm, between 650 nm and 700 nm, or above 700 nm.

In one aspect, the inner member comprises a convex, concave or non-planar surface for exerting pressure on the skin.

Also provided herein is a method to detect a change in blood microcirculation, comprising: reversibly applying an external force locally to one or more skin regions for a duration of time sufficient to alter blood perfusion in the skin region; providing one or more photonic excitation sources and one or more photonic detectors to measure one or more blood flow parameters in response to the external force before, during and/or after application of said external force; analyzing and quantifying the one or more measured blood flow parameters from said one or more regions of the skin; assessing said blood flow parameters to identify blood flow; and comparing the blood flow to one or more other assessments to determine the presence of a disease state. In some embodiments, the one or more photonic excitation sources and one or more detectors to measure one or more blood flow parameters in response to the external force, are used before the application of the external force. In some embodiments, the one or more photonic excitation sources and one or more detectors to measure one or more blood flow parameters in response to the external force, are used during the application of the external force. In some embodiments, the one or more photonic excitation sources and one or more detectors to measure one or more blood flow parameters in response to the external force, are used after the application of the external force. In some embodiments, the one or more photonic excitation sources and one or more detectors to measure one or more blood flow parameters in response to the external force, are used before and during the application of the external force. In some embodiments, the one or more photonic excitation sources and one or more detectors to measure one or more blood flow parameters in response to the external force, are used before and after the application of the external force. In some embodiments, the one or more photonic excitation sources and one or more detectors to measure one or more blood flow parameters in response to the external force, are used during and after the application of the external force. In some embodiments, the one or more photonic excitation sources and one or more detectors to measure one or more blood flow parameters in response to the external force, are used before, during and after the application of the external force.

In one aspect, the disease state is cancer. Cancer, in some instances can be skin cancer that is benign or malignant. In other instances, the cancer is metastatic.

In another aspect, the disease state is hypercholesterolemia, Alzheimer disease, carpal tunnel syndrome, schizophrenia, hypertension, renal disease, type 2 diabetes, peripheral vascular disease, atherosclerotic coronary artery disease, heart failure, systemic sclerosis, obesity, primary aging, sleep apnea, neonatal & adult sepsis, wound healing, or a combination thereof.

In the methods described herein, the one or more other assessments can comprise blood flow parameters measured in response to an external force applied to a skin region or regions. In one embodiment, the skin region comprises a lesion suspicious for cancer. In some instances, the reference skin region does not have cancer.

In such methods, the blood flow parameters are analyzed and quantified.

Analyzing the one or more measured blood flow parameters comprises utilizing multi exponential decay and rise functions; and life time distributions.

Assessing blood flow parameters relative to one or more other assessments can comprise comparing signal lifetimes and lifetime distributions obtained from the skin region with a reference skin region.

Analyzing the one or more measured blood flow parameters can comprise determining temporal relationships and correlations between signals acquired from a plurality of photonic detectors, where each receiver for a photonic detector is located at a different distance from the emission of the photonic excitation source.

Analyzing the one or more measured blood flow parameters can comprise determining temporal relationships and correlations between signals acquired from a plurality of photonic detectors at different wavelengths emitted from the photonic excitation source.

In such methods, the one or more blood flow parameters can provide a pressure-induced hemodynamic profile of the skin region, wherein pressure-induced vasodilation is determined from the shape of the pressure-induced hemodynamic profile, and wherein the pressure-induced vasodilation is indicative of the presence of the disease state.

The methods can further comprise performing hemodynamic analyses on a plurality of skin region locations, wherein the hemodynamic analysis of each location is compared to another location to determine or compare disease status.

Also provided herein is a method to detect changes in blood microcirculation, comprising: reversibly altering the temperature of one or more skin regions for a duration of time; using one or more photonic excitation sources and one or more photonic detectors to measure one or more blood flow parameters in response to the temperature alteration before, during and/or after alteration of the temperature of the one or more skin regions; analyzing and quantifying the one or more measured blood flow parameters from the one or more areas of the skin; and assessing said blood flow parameters to identify blood flow, and comparing the blood flow to one or more other assessments to determine the presence of a disease state. In some embodiments, the one or more photonic excitation sources and one or more detectors to measure one or more blood flow parameters in response to the external force, are used before the application of the external force. In some embodiments, the one or more photonic excitation sources and one or more detectors to measure one or more blood flow parameters in response to the external force, are used during the application of the external force. In some embodiments, the one or more photonic excitation sources and one or more detectors to measure one or more blood flow parameters in response to the external force, are used after the application of the external force. In some embodiments, the one or more photonic excitation sources and one or more detectors to measure one or more blood flow parameters in response to the external force, are used before and during the application of the external force. In some embodiments, the one or more photonic excitation sources and one or more detectors to measure one or more blood flow parameters in response to the external force, are used before and after the application of the external force. In some embodiments, the one or more photonic excitation sources and one or more detectors to measure one or more blood flow parameters in response to the external force, are used during and after the application of the external force. In some embodiments, the one or more photonic excitation sources and one or more detectors to measure one or more blood flow parameters in response to the external force, are used before, during and after the application of the external force.

Analyzing the one or more measured blood flow parameters can comprise quantifying amplitudes, temporal gradients and temporal shapes of hemodynamic profiles.

In one aspect, the disease state is cancer. Cancer, in some instances can be skin cancer that is benign or malignant. In other instances, the cancer is metastatic.

In another aspect, the disease state is hypercholesterolemia, Alzheimer disease, carpal tunnel syndrome, schizophrenia, hypertension, renal disease, type 2 diabetes, peripheral vascular disease, atherosclerotic coronary artery disease, heart failure, systemic sclerosis, obesity, primary aging, sleep apnea, neonatal & adult sepsis, wound healing, or a combination thereof.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3A is a cross sectional view where the disposable component 304 is configured to seat or guide the attachment of outer member component 301 through its bowl like structure. FIG. 3B is an end-on view; the structure of disposable component 304 has an opening enabling the inner member 302 to traverse through the outer member components and thereby contact the desired skin region (not shown) in order to accomplish blood removal and blood flow measurements.

FIGS. 4A-B are illustrative of a configuration of an outer member of a skin perfusion monitoring device having a handle. FIG. 4A: movement of slide button 403 in direction of arrow 420 will cause pin 414 to move down track 409 thereby causing spring 404 to move inner member downward in direction indicated by arrow 421, a translational motion. Distance of movement of inner member 401 into the skin and tissue 408 may be attributable to the strength (force) exerted by spring 404 and the relative stiffness or resistance to compression offered by skin and tissue 408. The result of such translational motion is shown in FIG. 4B. To return the inner member back to the initial state and to enable the tissue to decompress, slide button 403 may then be moved in the direction shown by arrow 416 in FIG. 4B.

FIG. 7B illustrates this point by presenting an array of photodetection elements 703 spaced about a single photonic source 702.

(FIG. 11B) a benign nevus, i.e., a mole; and (FIG. 11C) a confirmed basal cell carcinoma, BCC using a skin perfusion monitoring device.

FIGS. 12 A-D illustrate that signal dynamics are dependent on the wavelength of light used. FIG. 12C shows that, in general, both signal rise and recovery dynamics is slower at shorter interrogation wavelength (405 nm) as compared to dynamics at 590 nm (FIG. 12A, FIG. 12B) or 660 nm (FIG. 12D).

DETAILED DESCRIPTION OF THE INVENTION

Figure 1:
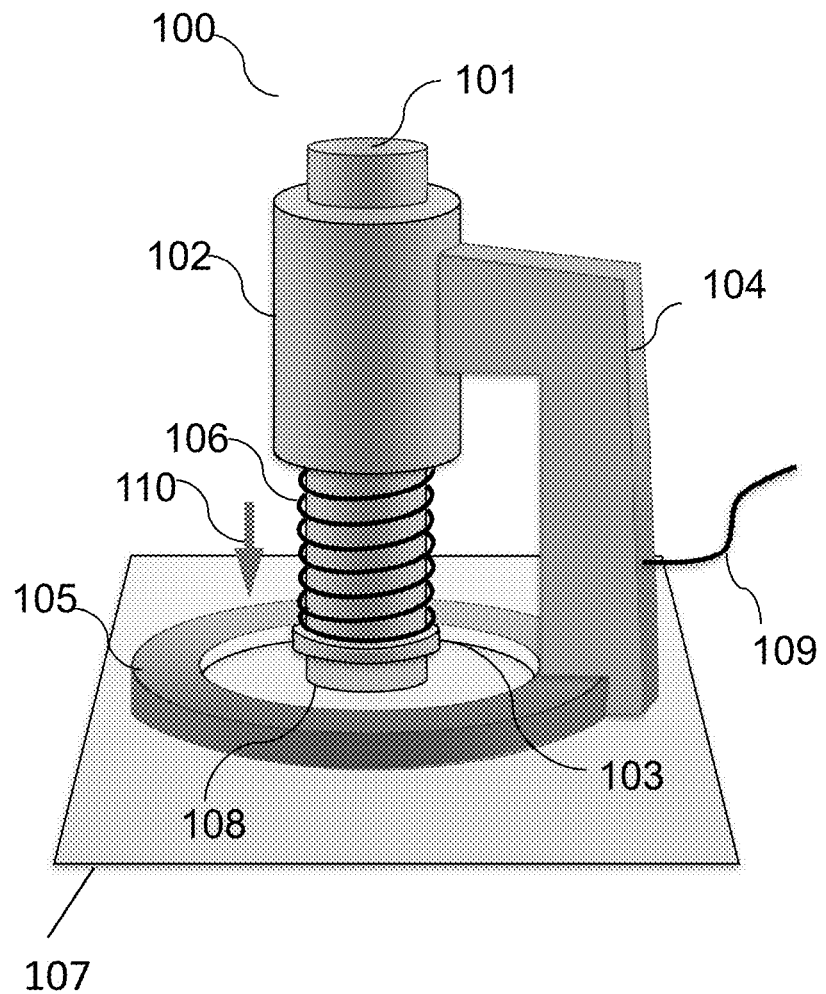
FIG. 1 is illustrative of an embodiment of a skin perfusion monitoring device.

Provided herein, in various aspects, are methods and devices for mechanical displacement of blood from a desired skin region followed by the reperfusion of blood into this region.

Skin microcirculation has been considered an accessible and potentially representative vascular bed to evaluate and understand the mechanisms of microvascular function and dysfunction. Vascular dysfunction (including impaired endothelium-dependent vasodilation) induced by different pathologies is evident in the cutaneous circulation. It has been suggested that the skin microcirculation may mirror generalized systemic vascular dysfunction in magnitude and underlying mechanisms. Furthermore, minimally invasive skin-specific methodologies using laser systems make the cutaneous circulation a useful translational model for investigating mechanisms of skin physiology and skin pathophysiology induced either by skin disease itself or by other diseases such as vascular, rheumatologic, and pneumologic diseases. To date, the skin has been used as a circulation model to investigate vascular mechanisms in a variety of diseased states, including hypercholesterolemia, Alzheimer disease, carpal tunnel syndrome, schizophrenia, hypertension, renal disease, type 2 diabetes, peripheral vascular disease, atherosclerotic coronary artery disease, heart failure, systemic sclerosis, obesity, primary aging, sleep apnea, neonatal & adult sepsis, wound healing, or a combination thereof.

Prior devices described suffer from the absence of adequate reference (control) signal making them sensitive to the type of tissue, physiological state and environmental parameters (e.g., temperature) which introduces significant error due to biological variability and requires complicated calibration and parameterization procedures. Examples include one such device as described by Howell (U.S. Pat. No. 3,698,382) wherein a platform system provides varying pneumatic pressure to a housing that is placed upon the skin. Within the housing are optical sensors intended to enable the determination of blood refill rates. As pneumatic pressure is varied, an assessment of capillary refill rate is then made using the optical sensors present within the device. Alternatively, Shani and Shavit (U.S. Pat. No. 6,685,635) describe a system having an external housing through which pressure is applied resulting in removal of blood from the depressed body region. As pressure is transitorily applied to the external housing, capillary blood refill is assessed using sensors located within the structure of housing. They also report the use of a temperature sensor to improve determination of skin capillary state and overall physiological status. A somewhat different approach is described by Messerges and Hutchinson (U.S. Pat. No. 8,082,017) which combines pulse oximetry with capillary refill time assessment. This device is designed to be placed upon the end of a patient's appendage, e.g., a finger or a toe. When affixed to the patient, one member of the device is located on one side of the appendage and a second member is located on the opposing side of the appendage. Pressure resulting in blood loss is then accomplished by an actuator located in one hinge resulting in both members compressing the intervening tissues.

None of these devices are specifically constructed as to enable a local determination of skin (capillary) blood perfusion enabling the definition of cancerous from non-cancerous skin tissue. That is, cancerous or precancerous lesions are often of the dimension of a few millimeters or less. Moreover, the described devices do not have a suitable shape to enable efficient displacement of blood from the area of interest.

The methods and devices disclosed herein overcome the shortcomings of the prior devices which is capable of determining with high spatial resolution of cutaneous blood, including relative capillary, displacement and refill rates over closely spaced area of skin, e.g., within a mole or suspect cancer growth as compared to an adjacent skin surface must be constructed towards this aim and dimensioned accordingly.

In some embodiments, displacement of blood results from a transitory pressure applied to the skin by one or more solid structures of a device, such as a device described herein, pressing on the skin region. In one embodiment, the device comprises an inner member and an outer member. In another embodiment, the structure utilized for pressure application is the inner membrane of the device. Reperfusion of blood into the skin region results upon the cessation of transitory pressure, due to the release of the compressive force. In an exemplary embodiment, the device utilized for pressure application comprises one or more sensors. The one or more sensors located, in some instances, within the structure utilized for pressure application (in some instances, an inner member) provide measurements of skin blood flow at one or more instances during performance of blood perfusion events (for example, no pressure, pressure, cessation of pressure). Data from such measurements can be employed for the determination of one or more parameters of blood flow dynamics (generally referred to as hemodynamics). Hemodynamic parameters, in various embodiments, correlate to a disease state. In one embodiment, the disease state relates to the physiology of the individual at the site of measurement, e.g., a skin cancer lesion. In another embodiment, a hemodynamic parameter is reflective of the health of an individual as a whole, e.g., cardiovascular status. In another embodiment, a hemodynamic parameter is reflective of the health of an individual with respect to, for example, hypercholesterolemia, Alzheimer disease, carpal tunnel syndrome, schizophrenia, hypertension, renal disease, type 2 diabetes, peripheral vascular disease, atherosclerotic coronary artery disease, heart failure, systemic sclerosis, obesity, primary aging, sleep apnea, neonatal & adult sepsis, wound healing, or a combination thereof.

Definitions

A malignant cancer is a cancer that has undergone characteristic anaplasia with loss of differentiation, increased rate of growth, invasion of surrounding tissue, and is capable of metastasis.

Metastatic cancer is a cancer at one or more sites in the body other than the site of origin of the original (primary) cancer from which the metastatic cancer is derived.

A tumor that does not metastasize is referred to as "benign".

There are several types of cancer that start in the skin. The most common types are basal cell carcinoma and squamous cell carcinoma, which are non-melanoma skin cancers. Actinic keratosis is a skin condition that sometimes develops into squamous cell carcinoma. Non-melanoma skin cancers rarely spread to other parts of the body. Melanoma is more likely to invade nearby tissues and spread to other parts of the body.

A melanoma is a malignant tumor of melanocytes which are found predominantly in skin but also in the bowel and the eye (uveal melanoma). It is one of the rarer types of skin cancer but causes the majority of skin cancer related deaths. Malignant melanoma is a serious type of skin cancer caused by uncontrolled growth of pigment cells, called melanocytes. Melanomas also include, but are not limited to, a choroidea melanoma, malignant melanomas, cutaneous melanomas and intraocular melanomas.

Melanoma may be divided into the following types: Lentigo maligna, Lentigo maligna melanoma, superficially spreading melanoma, acral lentiginous melanoma, mucosal melanoma, nodular melanoma, polypoid melanoma, desmoplastic melanoma, amelanotic melanoma, soft-tissue melanoma, and uveal melanoma. Melanoma stages are as follows:

Stage 0—melanoma in situ (Clark Level I).

Stage I/II—invasive melanoma: T1a: less than 1.00 mm primary, without ulceration, Clark Level II-III; T1b: less than 1.00 mm primary, with ulceration or Clark Level IV-V; and T2a: 1.00-2.00 mm primary, without ulceration.

Stage II—High Risk Melanoma: T2b: 1.00-2.00 mm primary, with ulceration; T3a: 2.00-4.00 mm primary, without ulceration; T3b: 2.00-4.00 mm primary, with ulceration; T4a: 4.00 mm or greater primary without ulceration; and T4b: 4.00 mm or greater primary with ulceration.

Stage III—Regional Metastasis: N1: single positive lymph node; N2: 2-3 positive lymph nodes or regional skin/in-transit metastasis; and N3: 4 positive lymph nodes or lymph node and regional skin/in transit metastases.

Stage IV—Distant Metastasis: M1a: Distant Skin Metastasis, Normal LDH; M1b: Lung Metastasis, Normal LDH; and M1c: Other Distant Metastasis OR Any Distant Metastasis with Elevated LDH.

In one embodiment, the methods described herein identify a melanoma or a likelihood, or risk of melanoma.

Additional steps or variations in the general method, such as the use of stepwise or incremental pressure, series of rapid pressures and releases, series of measurements, etc., may be employed within the overall scope of the devices and methods disclosed herein. Accordingly, the scope of the present disclosure is not limited to those series of steps or actions presented and exemplified here.

FIG. 1 presents an illustration of an exemplary blood perfusion device, 100. As shown, device 100 has inner member 101 enclosed substantially within a first component 102. The first component 102 is associated with a support component 104 and a base component 105. Collectively, components 102, 104 and 105 comprise the outer member of device 100 and are presented to generally indicate that an outer member of a device may be comprised of multiple components having a variety of functions. For example, the outer membrane component 102 is useful as a guide for inner member 101. As another example, outer membrane component 105 is useful to orient the device for positioning on a specific region of a skin surface 107. As another example, outer member component 104 is useful as a support, enabling the device to house electronics (not shown) and/or photonic sources (not shown) useful for device operation.

Also shown in FIG. 1 is wire 109 extending from outer member component 104. Wire 109 is shown to generally illustrate the functions that may be usefully present in such structures in various embodiments associated by having one or more external connections between device and one or more additional structures, etc. For example, wire 109 may represent an electrical power cord enabling the supply of power to device electrical components. Alternatively, the wire may represent a fiber optic cable transferring photonic energies to and from device 100 to an external unit having photonic energy sources and/or photonic energy receivers with associated electronics enabling signal analysis and processing. A third possibility is that wire 109 represents a data transference means, e.g., USB cable, between device 100 and a separate unit, e.g., a laptop computer or cell phone, enabling data analysis, device operational commands, and display of processed results.

Returning to inner member 101, inner member 101 may be configured to enable measurements of skin blood flow through one or more sensors (not shown) located in inner member 101 at component end 108, wherein 108 is a point of contact with a skin surface 107. Also contained within inner member 101 may be additional electronics, etc. to support the measurement of skin properties through one or more sensors located in end 108, and electrical wires, photonic guides and/or other forms of contacts enabling transference of power, data and/or photonic information between inner member 101 and outer member components 102 and 104.

Also shown in this general illustration is a spring 106 and a mounting ring 103 on inner member 101 that are presented to generally indicate the need to provide a means of exerting a small force on the skin surface 107 through the movement of inner member 101 towards and against the skin surface, as indicated by arrow 110. The purpose of this small force is to maintain the contact of the inner ring with the skin through all phases of measurement. Action of the spring 106 located between and in contact with inner member 101 and with mounting ring 103 results in a depressive force on the skin 107 through the pressure of the contact by end 108. The spring constant of spring 106 is chosen to be small enough so that the depression of the skin surface does not result in a forcing of blood from skin capillaries located in the immediate vicinity of this applied force.

Figure 7A:
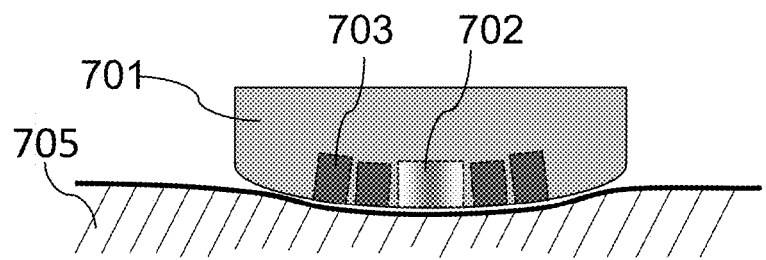
FIGS. 7A-B are illustrative of a sensor of the inner member of a skin perfusion monitoring device, wherein the sensor comprises a plurality of detectors and one light source. An example of the convex shape of the inner member structure is shown in FIG. 7A.

To enable application of force to the inner member, the component 102 may contain any means of applying the force to the inner member, i.e., an actuator or force transducer, for example: an electromagnet (solenoid), a linear motor, or pneumatic or hydraulic control. To be usefully applied, in an exemplary feature of the device, an opposing force resulting from the contact of inner member end 108 against the skin 107 is resisted by the structure and positioning of components of the outer member, collectively 105, 104 and 102. In one embodiment, it is desired that the applied force results in a depression of the skin surface (and associated removal of blood) rather than a lifting of the device or portions thereof from the skin; accordingly, the structures and operation of devices described herein are, in many instances, configured to enable this function. In this instance, device 100 may be held against skin surface by placement of one or more fingers on the outer top surface of outer member component 105, thereby through the strength of the hand enabling the depressive force exerted by inner member 102 to be successfully accomplished. In an exemplary device, the end of the inner member 108 is not subject to motion artifacts after the pressure to the inner member is released. Therefore the end of the inner member 108, containing sensing elements may be permanently attached to the inner member 101 or it may not be attached permanently. For example, 108 could be a component shown in FIG. 7 comprising light sources and detectors. As another example, 108 could be a component shown in FIG. 5; in this case the inner member 101 would apply force to feature 108 and then be retracted from 108, leaving 108 attached to the skin by means of adhesive forces. In the case 108 is not permanently attached to inner member 101, it could be connected by additional cables to enable electronics needed for feature 108 operation.

Figure 2:
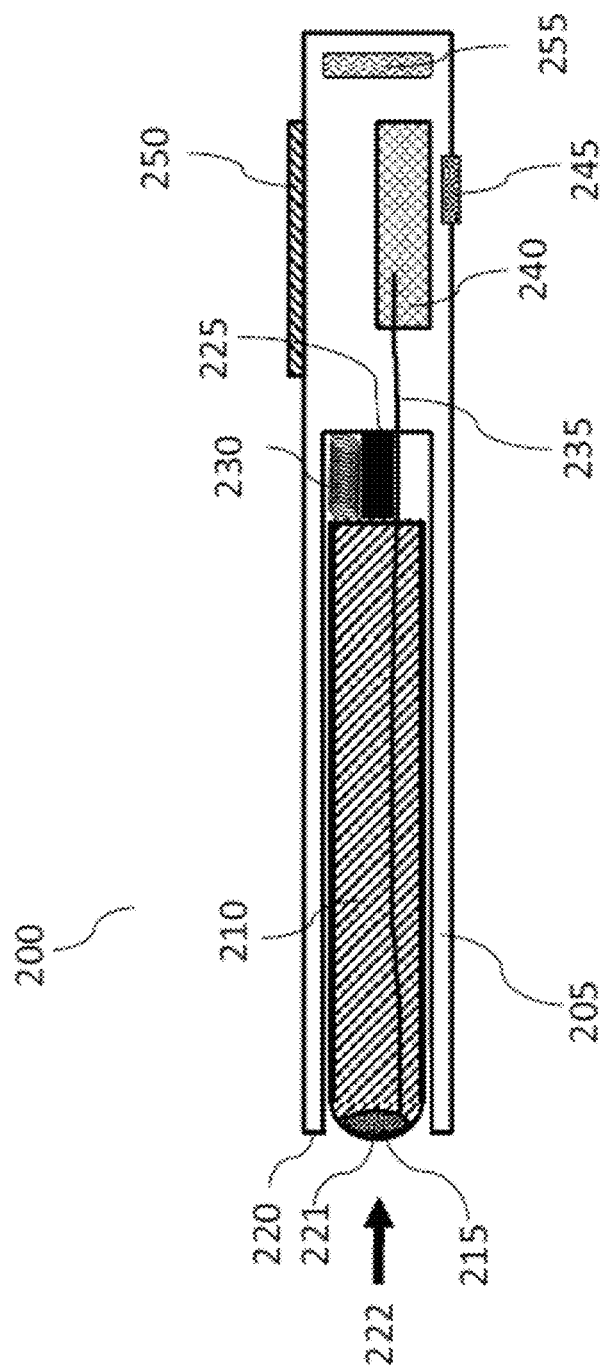
FIG. 2 is illustrative of an embodiment of a skin perfusion monitoring device depicting inner and outer members.

FIG. 2 provides an illustration of an embodiment of a device as provided herein. As shown, device 200 has an outer member 205 that substantially encloses inner member 210, except for an end opening generally indicated by arrow 222. A blood flow sensor head 215 is positioned at the end of inner member 210. Positioned between outer member 205 and inner member 210 is an actuator (e.g., a solenoid) 225 and a spring 230, enabling controlled piston-like movement of inner member 210 within outer member 205. Actuator 225 and spring 230 are intended to provide both extensive force (actuator 225) and retractive force (spring 230) to enable operation of the device, for example, inner member 210 exerts a depressive force on a skin region as the outer member 205 is positioned against the skin by hand. It should be noted that spring 230 is so configured as to enable retraction of the extended inner member while allowing continuous contact between the skin and the inner member.

In alternate embodiments, the outer member 220 may be affixed to skin, e.g., with use of a medical adhesive, or with belts, Velcro or straps to constrain its position and orientation with respect to skin surface. In certain instances, the structure affixing the outer member to the skin may itself be a portion of the device, e.g., as a separable disposable structure having an adhesive.

In yet other alternate embodiments, a plurality of inner members 210, sensor heads 215 and/or sensors located within sensor head 215 may be incorporated within device 200 in order to provide a plurality of measurements at one time.

Sensor head 215 at the end of inner member 210 is configured with one or more sensors (not shown) to enable measurement of skin physiological parameters when end opening 222 of device 200 is positioned against the skin. In correct use, device end opening surfaces 220 and 221 are positioned to be substantially in contact with the skin in order to enable pressure variation to be applied to the immediate skin area and measurements of skin blood perfusion to be obtained while doing so. Sensor signals so obtained are conveyed between electronics 240 and sensor head 215 by connector 235.

Also shown within device 200 are operating switch 245, battery 255 and display 250 to enable operation of device 200. Battery 255 may be replaceable, rechargeable, or in certain instances, power to device 200 may be supplied by an external power source, e.g., electrical outlet connected to the device.

Not shown in FIG. 2 are necessary electrical and connections (e.g., optical connections) between the various components of the device 200 to enable their functionality. It will be readily appreciated that such electrical connections as well as electronic circuitry contained within electronics 240 are well understood by those skilled in the art of electronic circuitry.

It may be readily appreciated that the control of mechanical motions and photonic signal delivery and acquisition may be accomplished in a variety of ways and are not constrained to the examples and device component configurations presented here.

Device Operation

In an exemplary mode of operation, a device of the present disclosure, for example, such as one illustrated in FIG. 2, is first positioned on a region of mammalian skin wherein the area to be measured is in contact with end surface 221 of inner member 210. At least a portion of the corresponding end surface 220 of outer member 205 thereby is also caused to come into contact with skin surface. In addition, inner member 210 is so constructed to aid in the shielding of photonic sensors contained in sensor head 215 from stray or non-intended energy sources, e.g., stray light.

The operator of the device then activates the device using switch 245. Activation results in electrical power being supplied from battery 255 to electronics 240 and other components, e.g., actuator 225 and display 250, as directed by electronics 240. Upon activation, inner member 210 is mechanically moved in an outward direction relative to outer member 205, e.g., by actuator 225. In various embodiments, the force utilized to move inner member 210 may be by means other than an actuator, e.g., electromagnet, electroactive polymers, or pneumatic pressure supplied by an external source, manual means, etc., and the scope of the present disclosure is not constrained to any one means of applying a translational force to inner member 210.

The translational motion of inner member 210, while outer member 205 remains positioned in substantial contact with the skin at surface 220, results in mechanical force being applied to the immediate skin surface. As a result, skin vasculature in the immediate area is compressed, resulting in an outflow of blood from the compressed region. It is readily understood that sensor head 215 is advantageously positioned at the end of inner member 210 to perform measurements upon local skin blood flow throughout this process.

In many implementations, it is a desired feature that the structure or mode of operation of the inner member may be such that blood removal from the compressed skin region is facilitated. This may include the shape of the surface that contacts the skin being, e.g., convex rather than planar such that blood is progressively moved from the region as more of the inner member contacts the skin. Examples of the convex shape of the inner member structure are shown in FIG. 2, FIG. 5, FIG. 7A and FIG. 8. For example, FIG. 2 shows the rounded end 221 of inner member 210.

In an alternative embodiment, the device or inner member may be applied at an angle to the general plane of the skin and then shifted to an orientation generally at right angles to the skin during the application of pressure. Additional means or inner membrane shapes facilitating blood removal are conceivable and the scope of the present disclosure is not limited to these examples.

As alternate applications, the structure or mode of operation of the inner member can be chosen to increase the amount of blood in the compressed region. This may include having a shape of the surface of the inner member in contact with skin that is concave such that blood is trapped by the edges and progressively pushed toward the center of the compressed area where the sensing area is located.

After transitioning a certain distance, movement by inner member 210 relative to outer member 205 ceases. This distance may be a predetermined distance, e.g., a predetermined distance relative to outer member 205. The travel of inner member of this predetermined distance may be governed by a variety of means, e.g., through actions of actuator 225 under the control of one or more sensors able to discern distance travelled or electronic timing present within electronics 240.

In alternate embodiments, the distance traversed by inner member 210 may be governed by one or more sensors able to discern one or more physiological parameters associated with the desired outcome of motion, e.g., the partial or complete removal of blood or increase in the amount of blood in the skin region under compression and thereby facilitate automated operation of the device. Examples of such sensors include pressure transducers so positioned within device 200 or on the device 200 surface as to sense the pressure applied by inner member 210 to skin surface. Such sensors may be present on the inner member 210, outer member 205 or both, the scope is not constrained to any one location. The scope of the present disclosure is not constrained to any one form or method of determining distance traversed.

Such distance sensors may also include those sensors utilized for making determinations of the blood present in the compressed region. That is, by a determination of change in amount of blood (e.g., blood removal), a feedback signal from said blood sensors to electronics may then be used to govern the means used to move inner member 210, e.g., control the actuator 225.

In addition, pressure sensors located on the outer member in contact with the skin surface may be utilized to ensure that outer member 205 remains in substantial contact with skin surface but is not applying by itself an undesired level of pressure to the local skin area. Readings from such sensors may be sent to display 250 to enable the individual using the device to more appropriately position the device on the skin surface.

Upon ceasing movement, inner member 210 may remain stationary relative to outer member 205 and thereby hindering local blood flow in the compressed region for either a short duration, e.g., <1 second, or longer. Longer durations may advantageously enable the establishment of a plurality of measurements to which either prior or subsequent measurements may be compared.

After the desired time period has passed, the force applied to the inner member 210 is turned off resulting in the inner member being rapidly retracted back into outer member 205. In preferred embodiments, this retraction may be the result of cessation of actuator activation and resulting from tissue-compression force pushing the inner member 210 back towards original position with a spring 230 useful in maintaining the surface of inner member 221 to remain in effectively continuous contact with the skin. In alternate embodiments, other methods for retracting inner member 210 may be employed, e.g., vacuum or manual, and the scope is not constrained to any one means of moving inner member 210 back within outer member 205.

In one embodiment, after returning the inner member 210 to the original position relative to outer member 205, blood measurements utilizing sensors located in sensor head 215 may continue for either a predetermined or arbitrary length of time. In another embodiment, during and after returning the inner member 210 to the original position relative to outer member 205, blood measurements utilizing sensors located in sensor head 215 may continue for either a predetermined or arbitrary length of time. The methods and devices provided herein are not constrained to any one measurement period.

It is a desired feature that the rate of travel and distances traversed by inner member 210 relative to outer member 205, upon release of the applied force, does not exceed the elasticity present in the measured skin region and thereby cause an interruption in the measured skin signals. In such instances, wherein the rate of travel and distances are congruent with the rebound elasticity of the compressed skin region, sensor head 215 and its end surface 221 remain in substantial contact with the skin surface throughout these motions.

In certain instances, the entire device may be pressed against the skin, e.g., pressure applied outer member 205 also resulting in local blood loss in the skin area in substantial contact with outer member 205. In such instances, useful data may be obtained by examining the relative effect of inner member 210 further locally compressing the skin region in a reversible fashion.

Alternatively, when an external force to apply pressure using outer member 205 is employed, the inner member 210 may be configured or commanded to not move in relationship to the outer unit. Such a result may be obtained by an electronic command instructing the inner member not to move.

In related embodiments, the device may be effectively constructed as a single unit whereby the inner member and outer member form effectively a single contiguous structure. In such embodiments, needed force (e.g., pressure) for blood removal may be applied through a separate mechanism, e.g., mechanical (by hand), hydraulic or pneumatic mechanisms applied to entire structure 200. In yet still other embodiments, in a device having an effectively solid structure, the device can be securely fixed to the skin region and the user transiently applies pressure by hand for sensing purposes.

In alternate or additional embodiments, a device comprises a plurality of inner members and at least one outer member. In such configurations, a plurality of skin surfaces may be measured in effectively a simultaneous fashion. Such plural forms of the device may be advantageously employed where a suspect lesion is measured during the same measurement period as a non-suspect (control) skin area is measured, without the extended time period required by sequential measurements.

In yet other configurations of the device, the outer member may have at least one element separable from the inner member.

In such embodiments, the outer member may be comprised of one or more separate components, e.g., an adhesive strip having one or more alignment marks to aid in positioning of the inner member and a separate ring or guiding structure to enable the placement of the inner member in a position in accordance with the adhesive strip alignment marks. In yet other embodiments, the outer member may have a conformable portion or separable component, e.g., sponge or soft rubber, element that contacts the skin to promote both good contact of the device with the skin and to provide comfort to the user. Additional forms and types of the structure of the outer members are readily conceivable and therefore the scope of this disclosure is not restricted to the examples and configurations presented herein.

It will be readily appreciated that one or more measurements concerning the presence of blood in the measured region may be made at various points in the measurement cycle. In preferred embodiments, such measurements are made in an effectively continuous fashion, e.g., once every 10 milliseconds, such that a contiguous data set describing local blood removal and reperfusion is obtained enabling detailed characterization of the blood flow dynamics. Data from one or more measurements may then be analyzed to ascertain the likelihood or presence of a disease state.

Exemplary elements of a blood perfusion device are described in greater detail below.

Outer Member

Provided herein, in various aspects, is a blood perfusion device comprising an outer member and an inner member, wherein the device is configured to measure at least one blood flow parameter from a skin region. A primary function of the outer member is to serve as a guide or support to enable the proper positioning and operation of the inner member. As such, in one embodiment, the outer member has at least one surface region in substantial contact with a region of skin proximal to the skin area to be depressed by the inner member and at least one surface portion able to contact at least a portion of the inner member. In an additional embodiment, the outer member, once positioned against the skin region as a first step in the measurement process, is intended to be relatively stationary during the remaining steps of the measurement process, e.g., remain immobile against the skin, thereby aiding in the guiding of the inner member during its motions relative to the removal and reperfusion of blood from the measured region. Upon completion of the measurement process, the outer member may be then removed or lifted from the skin surface. This removal may also be coincident with the removal of the inner member, dependent on the exact configuration of the device.

In structure, an exemplary form of the outer member is one that (a) is at least partially conical or cylindrical in overall shape, wherein the inner member is enclosed circumferentially, at least in part, by the outer member and (b) has a surface that may contact the inner member at least at one location via one or more contact points. In many embodiments, such contact points enable the guiding of the inner member to a specific skin location for the application of pressure. In such embodiments, the outer member may have an opening through which the inner member may pass to cause the pressure necessary for blood removal from the skin region.

In other embodiments, the outer member may have a shape other than cylindrical or conical, e.g., rectangular or C shaped, or even have a shape whereby the inner member is not substantially encircled by the outer member, e.g., the outer member is configured as a linear rail or guide that is configured to serve as a guide to the inner member during inner member operation.

In these and other embodiments, the outer member may be comprised of separable components. For example, at least a portion of one component of the outer member may be a ring or similar conical structure in contact with the inner member. A separate component of the outer member may be in the form of a transparent tape. In this embodiment, the tape may serve as an interface between the skin and the other components of the device, e.g., the other portions of the outer member and the inner member.

Figure 3A:
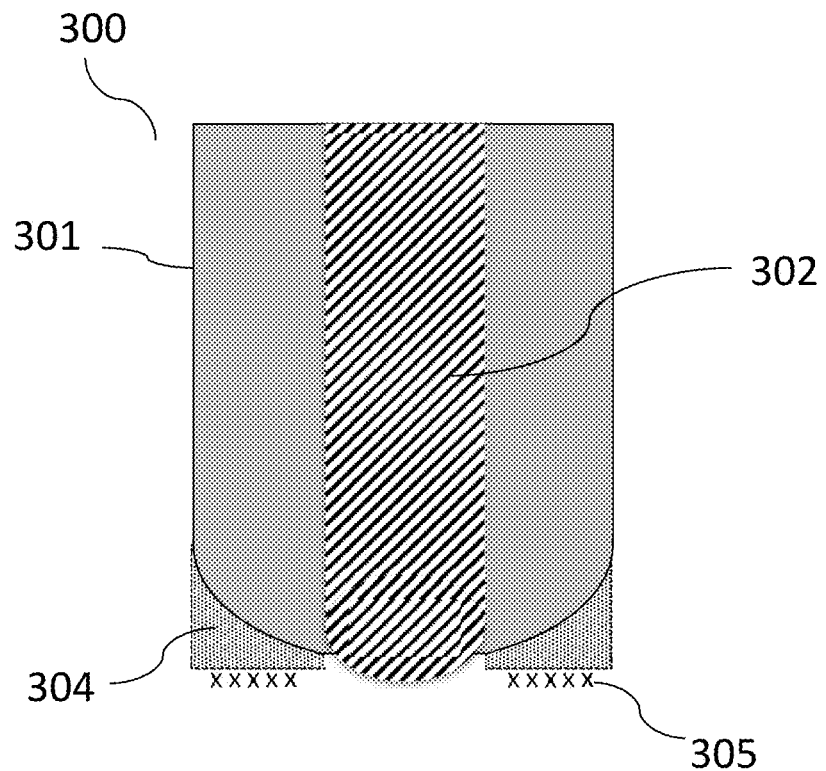
FIGS. 3A-B are illustrative of one configuration of an outer member of a skin perfusion monitoring device.
Figure 3B:
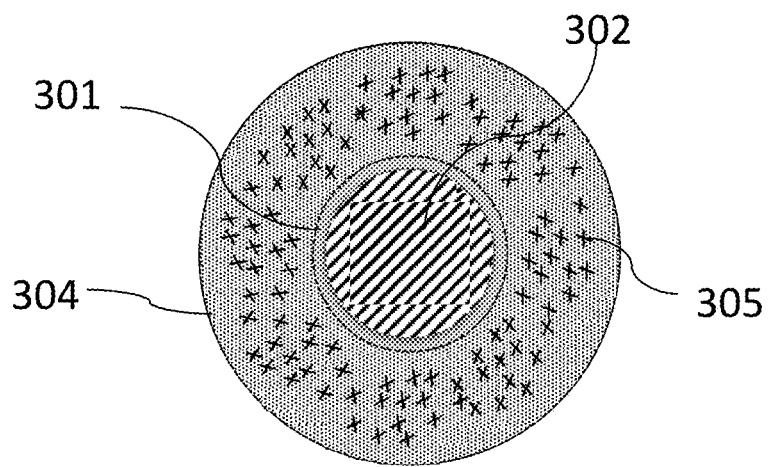

In a related or additional embodiment, the outer member has a separable component that has both a guiding function as well as an adhesive function. FIG. 3 presents an example of one such embodiment. FIG. 3 presents a section of a device 300 having an outer member component 301 in contact with inner member 302 and disposable outer member component 304. Disposable component 304 has adhesive 305 to facilitate the positioning and adhesion of device 300 to the skin in a desired location. As shown in FIG. 3A, a cross sectional view, the disposable component 304 is configured to seat or guide the attachment of outer member component 301 through its bowl like structure. As shown in FIG. 3B, an end-on view, the structure of disposable component 304 has an opening enabling the inner member 302 to traverse through the outer member components and thereby contact the desired skin region (not shown) in order to accomplish blood removal and blood flow measurements.

In such instances as those illustrated in FIG. 3, a separable component may be constructed as a disposable component such that it may be employed on a single use basis. A desirable feature of such embodiments is that the disposable component may be positioned onto the skin in advance of the attachment to this disposable component by the other portions of the outer member by the operator.

One requirement for such separable components, e.g., a tape, collar or other disposable component, is that it be so constructed as to enable the operation of the inner member, e.g., the application of pressure to the skin by the inner member and/or the measurement of blood within the skin by one or more sensors located within the inner member. In those instances wherein a separable component, such as a tape, intervenes between the skin surface and a device component such as an inner member having motion and/or sensing capabilities, in many embodiments, it is desired that the separable component be relatively thin (e.g., less than 0.2 mm in thickness) and conformable or stretchable to the movements and applied pressures by the device component (e.g., inner member) as well as able to pass signals employed in measurement (e.g., the separable component is effectively transparent to the wavelengths of light utilized for photonic measurements). In one embodiment, separable component 304 is made of a flexible material that can easily compress to conform to a convex probe head shape of a device component (e.g., outer member).

In certain instances, an outer member is constructed to be affixed to the skin and then disposed of after use. In one embodiment, this disposable outer member may also contain one or more blood sensors, e.g., photonic sources and/or photonic receivers. In such instances, the inner member may serve as a mechanical means enabling pressure application for blood displacement and/or reperfusion from the measured region. For embodiments such as these, sensors may be fabricated or positioned within a tape or other separable component using one or more methods of construction, such as printed electronics, whereby the circuitry elements and sensors are effectively printed into the structure of the separable component, e.g., the tape.

The outer member, in various embodiments, is configured to enable the positioning of the device by hand on the intended region of the skin of an individual for blood perfusion measurement. Accordingly, all or a portion of the outer member may be constructed in the form of a handle or similar structure enabling its manual placement and operation. For example, a device with the outer member in the shape of a pen or rod-like structure generally sized between about 7 centimeters and about 15 centimeters in length and from about 1 centimeter to about 4 centimeters in approximate diameter would enable clasping of the outer member of the device by hand for use in positioning and device operation. It would be understood that alternate sizes and holding arrangements are conceivable and the dimensions of the device are not restricted to those described here.

Alternatively or additionally, the outer member may be constructed with differing functional sections. That is, a portion of the outer member may be configured to be held by a hand, while a separate portion of the outer member is configured to interact (e.g., as a guide and/or as an anchoring point for forces to be applied) with the inner member. For example, an outer member having a handle extending at roughly a 90° angle to a roughly conical portion of the outer member, wherein the outer member interacts with the inner member, is illustrated in FIG. 4.

As shown in FIG. 4, device 400 has outer member components 402 and 405 and an inner member 401. Not shown are sensors, electronics, power, etc. needed for device operation. However, one can readily envisage the ability to put such elements within this device by one skilled in the art of medical device construction. Outward motion of inner member 401 relative to outer member 402 is achieved through means of spring 404 contacting outer member 402 at base structure point 410 and contact notch structure 422 on inner member 401. Governing the outer motion is slide button 403 connecting to structure 415 that contains pin 414 in track 409 located in the outer member 402.

As shown in FIG. 4A, movement of slide button 403 in direction of arrow 420 will cause pin 414 to move down track 409 thereby causing spring 404 to move inner member downward in direction indicated by arrow 421, a translational motion.

Distance of movement of inner member 401 into the skin and tissue 408 may be attributable to the strength (force) exerted by spring 404 and the relative stiffness or resistance to compression offered by skin and tissue 408. The result of such translational motion is shown in FIG. 4B. To return the inner member back to the initial state and to enable the tissue to decompress, slide button 403 may then be moved in the direction shown by arrow 416 in FIG. 4B. Such movement will result in structure 415 moving pin 414 upwards against spring 404, thereby removing the downward force of spring 404 on inner member 401. The release of this downward force will enable the skin and tissue 408 to push back against inner member 401 in the direction of arrow 417.

In various instances, it may be desirable to facilitate this return motion shown by arrow 417. In particular, such facilitation may enable various masses of inner member 401 to be employed without deleteriously affecting measurements, e.g., having too great a mass of inner member 401 to allow skin and tissue to decompress readily. To achieve this return motion, structures such as spring 407 may be employed. As shown, spring 407 extends between outer member 402 and inner member contact point 406. Upon outward motion of inner member 401, spring 407 compresses. If the strength of spring of 407 is selected to be lesser than the strength of spring 404, then net movement outward will occur, until skin and tissue resistance stops this outward movement. Upon removal of the downward force of spring 404, e.g., by actions of slide button 403 in the direction of arrow 416, spring 417 will aid the skin and tissue 408 in the movement of inner member back into the device 400.

In various embodiments, the point(s) or elements of contact between the inner member and outer member function to facilitate the movement of the inner member relative to the outer member. Such a function may be in addition to the point of contact serving as a guide for the inner member. To enable the relative motion of the inner member, the point(s) of contact may be configured in a variety of forms, e.g., in the form of a gear, an electrical element within a solenoid-type arrangement between the inner and outer member, a mechanical spring attachment point, a seal enabling the use of pneumatic pressures, or various combinations of these or other methods of power or force transference.

In many embodiments, the outer member is intended to be positioned and held against the skin at a desired body location. Upon device activation and through the relatively stationary positioning of the outer member (as held by hand or adhesive), the activation of the translational mechanism thereby enables the motion of the solid inner member to apply pressure to the skin. This pressure depresses the skin and tissues in the contact region and results in the forced removal of blood from the immediate skin region due to this applied pressure. It is desirable in most instances that the applied pressure exceeds the filling pressures typically provided by the blood vasculature to the skin capillary and arteriole networks such that blood is prevented from flowing into these capillary beds and is also forced from them into the surrounding venous system.

In various embodiments, the forces applied by and/or distances traversed by the inner member may be such that deeper capillary and vascular systems are affected, e.g., resulting in blood flow being prevented to or forced from these vascular structures. In such instances, additional measured data may be obtained from deeper tissue regions useful for the diagnoses of a disease state, e.g., the degree of skin tumor invasiveness into a deeper tissue structure.

In other or additional embodiments, the force to enable the translational motion of the inner member relative to the outer member is supplied by hand and point(s) of contact serve purely to guide the translational motion of the inner member. That is, one hand may hold the outer member in position against the skin while a second hand applies force to the inner member causing the inner member to move. In such instances, the inner member or structures associated with the inner member may project through more than one opening in the outer member, e.g., one opening for the point of contact with the skin and one opening for contact with a hand or other external force applying structure.

In still other embodiments, the outer and inner members are immobilized relative to each other such that force applied to the outer member results in pressure being applied to the skin by the inner member. In such instances, the outer member may be structurally indistinct from the inner member, i.e., the inner member is distinguished by the presence of one or more sensors and the outer member has one or more circuitry elements needed for data measurement and display, wherein both the inner and outer members are housed within the same overall shell or covering.

In various embodiments, the outer member and/or inner member may also contain components or structures enabling the transference of data, processed data, power and/or sensor (photonic) energy to and/or from a unit separate from the device. For example, the outer member or inner member may be configured for attachment to a USB cable enabling transference of measured data with a separate unit, e.g., a cell phone, for control/operation instructions, signals, additional data processing and display of results. In an alternate example, the outer unit may be configured for attachment to a fiber optic cable, enabling the transference of photonic energy to and from the outer member and then to the inner member and/or sensors. In still another example, the outer member or inner member may be configured as a tube enabling the transference of pneumatic power from an external pump to the outer member, thereby supplying a source of pneumatic force useful for the application of pressure by the inner member against the skin. In still other instances, the pneumatic pressure source may be in the form of a cartridge located in the outer member and pressures applied onto the inner member are governed through the use of various valves and seals.

In additional or other embodiments, the outer member or inner member may comprise one or more controls and/or display or alerts. Examples of these may include one or more on/off switches or buttons for initiating and/or operating the device, one or more indicator lights indicating the operational status of the device, one or more audible alerts indicating the status of the device or instructional activities to be performed, one or more small displays configured to display operational status, data and/or the results of data process, and any combination thereof.

The outer member may be constructed of a variety of materials, e.g., plastics, rubbers, metals. The outer member may have electronic circuitry, batteries, lights, displays, etc. The exact composition of outer member materials is dependent on the nature of the device embodiment and functional needs. Creating such constructions are well known to those skilled in the art of medical device construction.

Inner Member

Provided herein, in various aspects, is a blood perfusion device comprising an outer member and an inner member, wherein the device is configured to measure at least one blood flow parameter from a skin region. In various embodiments, a primary function of the inner member is to mechanically exert pressure onto a desired skin or tissue region resulting in the forcing of blood from capillaries in the immediate vicinity of this applied pressure, i.e., a blanching of the skin caused by pressure. In exemplary embodiments, this mechanical transmission of pressure is accomplished by the movement of an effectively solid or rigid surface against the skin or tissue region, wherein the surface is associated with at least a portion of the inner member. In preferred embodiments, such pressures are those sufficient to result in a cessation of flow into the capillary bed and/or associated arterioles, and are generally assumed to be in the vicinity of 4 kPa, or in general, in excess of the internal pressure associated with capillary flow, e.g. approximately 4 kPa or 32 mm Hg. In alternate embodiments, the applied pressure may be greater, lesser or varying, in order to execute the desired removal and subsequent reperfusion of blood in the measured region. In one embodiment, the pressure is from about 1 kPa to about 400 kPa, from about 2 kPa to about 400 kPa, from about 3 kPa to about 400 kPa, from about 80 kPa to about 400 kPa, from about 5 kPa to about 400 kPa, from about 4 kPa to about 400 kPa, from about 4 kPa to about 400 kPa, from about 1 kPa to about 350 kPa, from about 1 kPa to about 300 kPa, from about 1 kPa to about 250 kPa, from about 1 kPa to about 200 kPa, from about 1 kPa to about 150 kPa, from about 1 kPa to about 100 kPa, from about 1 kPa to about 50 kPa, from about 2 kPa to about 100 kPa, from about 3 kPa to about 75 kPa, or from about 3 kPa to about 50 kPa.

In general terms, application of pressure via the motion of the inner member against the skin results in depression of the skin and underlying tissue. In part, the distance or depth of the depressed region is dependent upon the compliance or stiffness of the tissues underlying the immediate skin region. For example, a skin region having a bone or bone-like structure immediately beneath will exhibit greater resistance (after an initial depression of a few microns to millimeters) than a skin region overlaying soft tissues such as an abdominal region having an excess of subcutaneous fat. Accordingly, the present methods and devices disclosed herein are not restricted to any one distance of movement, and may range from fractions of a millimeter to several millimeters or centimeters, dependent on the device embodiment and the skin region examined.

In order to accomplish said desired pressures and movements of the inner member, it is a desirable feature of various device embodiments that the inner member be constructed, at least in part, in the form of a solid structure enabling the transference of applied power and motion from the outer member to the skin region via the inner member. Such inner member structures may include, but are not limited to, structures in the form of rods, closed cylinders, spheres, inflate-able bags (pneumatic or hydraulic), electro-active polymers configured for translation elongation, or structures comprised of substances capable of phase transitions which upon conversion, e.g., from liquid to solid, result in a change in the overall dimensions of the structure.

Overall, the region of skin to be compressed is desired to be of a dimension suitable for the measurement of cutaneous blood flow (e.g., skin capillary blood flow) during a process described herein (e.g., applied and/or removed pressure to the region) by the sensor methodology employed. Accordingly, the dimensions of the skin contact region (and corresponding inner member surface) are, in various embodiments, preferably greater than that represented by a single capillary, i.e. 6-8 microns in cross section. In many embodiments, a desired function of the device, in part, is the ability to distinguish between normal capillary networks and those associated with cancerous tissues, wherein the dimensions of the contact region are therefore more preferably greater than that of a single capillary. Accordingly, in many embodiments, the dimensions of the skin contact region and of the corresponding surface of the inner member are at least 0.1 mm2 in area.

In exemplary embodiments, the shape of the inner member that contacts and compresses the skin region (or contacts a portion of an outer member, e.g., a tape, intervening between the inner member and the skin region) is configured to facilitate the movement of blood from the compressed skin region. The present inventors have discovered that the movement of blood from the skin is facilitated by the use of a rounded (convex) surface to apply pressure to the skin, as opposed to a stiff, planar surface that tends to pool blood within the region of applied pressure; moreover we have demonstrated that using flat or concave surface to apply pressure to the skin tends to lead to the accumulation of the blood within the region of applied pressure. In alternate embodiments and for the diagnosis of different disease states, it may be advantageous to use a concave inner membrane and/or sensor surface.

Accordingly, in exemplary embodiments, the shape of the inner member surface is configured to facilitate the movement of blood from the approximate center of the skin contact region to the periphery as translational motion is applied. For example, the inner member surface has, e.g., a convex shape such as spherical or parabolic surface and is of sufficient rigidity to enable effective pressure to be applied. In various embodiments, this movement of blood from the region may be further facilitated by a slight rocking motion or inclination of the inner member during compression.

In an additional embodiment, the inner member serves as a support or structure housing one or more sensors which enable the determination of blood flow in a measured region of skin. In an exemplary embodiment, such sensors comprise at least one source of photonic energy, to be applied to the skin region, and at least one means, e.g., waveguide, fiber optics, etc., of receiving one or more photonic energies from the skin region. A non-limiting example of such an arrangement is shown in FIG. 5.

Figure 5:
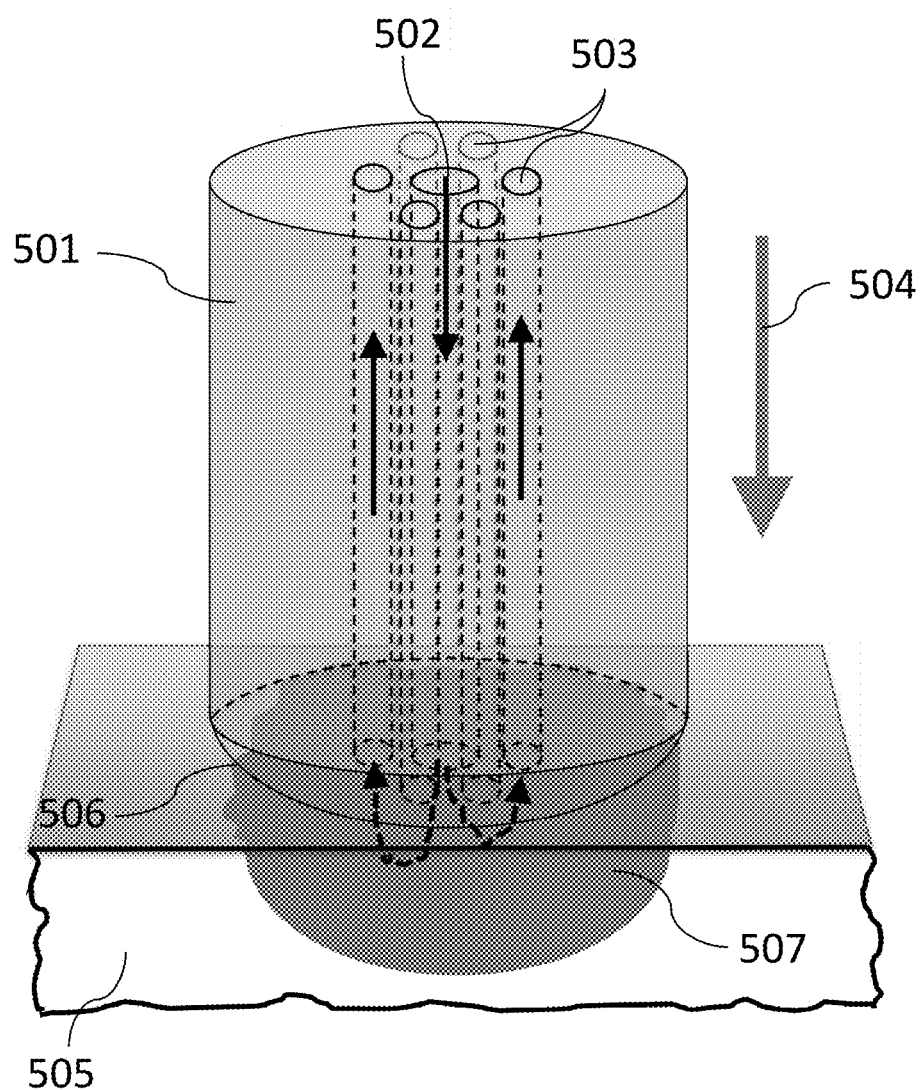
FIG. 5 is illustrative of one configuration of an inner member of a skin perfusion monitoring device.

FIG. 5 illustrates a section of an exemplary inner member 501, having rounded tip 506. Within inner member 501 is fiber optic 502 providing photonic energies to a skin tissue region 507 located within larger skin tissue region 505. Photonic energies so delivered may scatter and be absorbed in region 507. A portion of these energies may in turn encounter return fiber optics 503, conveying these photonic signals to one or more photodetectors located elsewhere in the device, as shown by arrows directed upward. The controlled movement of inner member section 501 in the direction of arrow 504 results in the measurement of a blood flow parameter from tissue region 507 during the conditions associated with tissue compression and the forcing of blood from this region.

One may readily envisage embodiments where a plurality of photonic energy sources and/or photonic energy signal receivers (photodetectors) are utilized to better inspect larger skin regions and/or comparatively assess under the same measurement cycle various discrete skin areas within a larger site of measurement. For example, if a desired function of the device is to delineate the margins of a tumor, then by use of an array of sources and detectors, e.g., employing multiple fiber optic cables with multiple sources and photodetectors, one might effectively image the boundary or signals associated with the transition of capillary types associated with cancerous tissue versus normal tissue.

In order to accomplish the desired functions of the inner member, the inner member may be composed of a variety of materials and components. For example, materials such as plastics, rubbers, metals such as stainless steel, aluminum, brass, may be employed in various combinations in order to configure the inner member according to the requirements of that embodiment of the device.

In alternate or additional embodiments of the device, the inner member can be used alone without the outer member. In such a case the inner member would preferably be a short, round or square part, for example as the part 701 depicted in FIG. 7. In one embodiment, the surface of 701 in contact with the skin comprises an adhesive coating or an adhesive consumable part which would maintain the surface 701 in the contact with the skin throughout a measurement of a blood flow parameter. The pressure would be applied manually by, e.g., pressing by the hand onto the upper surface of the 701. Such configuration is advantageous as it reduces contributions from motion artifacts after the force is released.

Sensors

Provided herein, in various aspects, is a blood perfusion device configured to measure at least one blood flow parameter from a skin region using one or more sensors. In various embodiments, the sensor comprises an energy source or transmitter, such as a photonic excitation source. In various embodiments, the sensor comprises an energy receiver or detector, such as a photonic energy signal receiver or photodetector. In some embodiments, the sensor is a component of an inner member of the device. In other or additional embodiments, the sensor is a component of an outer member of the device. In some embodiments, the device comprises a plurality of energy sources. In other or additional embodiments, the device comprises a plurality of energy receivers or detectors. A principal element of the device of the present methods and devices disclosed herein is the incorporation of at least one sensor intended for the measurement of a blood flow parameter, including, but not limited to, blood volume and perfusion rates in the measured body region, e.g., the skin capillary blood vessels. In general, such sensors may utilize the transference of one or more energies to and from the body region where such energies are chosen based upon their interaction with one or more aspects of biological tissues appropriate for the determination of skin capillary blood perfusion.

Generally, such energies are preferably supplied to the immediate body region by a transmitter located in or on the device. Following interaction with one or more body tissues, structures and/or chemical components, a portion of the non-absorbed energy may then be radiated back from the body region to be received by a receiver on the device. The resultant data may then be analyzed for signals associated with one or more components of blood, e.g., hemoglobin, or blood vessels, associated with capillary blood perfusion.

In preferred forms of the methods and devices disclosed herein, such energies are photonic in nature, e.g., signals at one or more visible wavelengths that are absorbed, in part, by chromophores contained within the hemoglobin of blood. In order to supply such photonic energies, a source such as a light emitting diode is typically employed. Such sources advantageously provide light centered about a single frequency, e.g., 590 nm±20 nm or 420 nm±20 nm, which may be selected for its sensitivity to one or more blood components and/or insensitivity to other biological structures or chemical compounds within the skin or to enable measurement at various depths in the tissue (see below).

Such ranges of light may be obtained by use of one or more filters within the light path from the light source to the detector, e.g., as a band pass filter position in front of the photodetector, or photonic detector, element of the device. Such positioning may also advantageously limit the introduction of unwanted light to the photodetector where such light arises from a source other than that of the device, e.g., light at other wavelengths arising from light sources present elsewhere, such as a room light. In addition, the use of filters assists in assuring that intended photonic energies are measured, e.g., filters that only enable polarized light to pass may be employed within various embodiments of the device.

It should be understood that a variety of chromophores are present within biological tissues including blood and accordingly, the scope of the present methods and devices disclosed herein is not restricted to any one wavelength or wavelengths for the determination of blood presence within the measured region. Likewise, a plurality of photonic energies, i.e., different wavelengths, may be employed to enable more detailed analysis of the capillary blood perfusion. In certain instances, such different wavelengths may be selected to enable various depths of measurement, i.e., certain frequencies penetrating to deeper tissue regions than others, to enable a three dimensional interpretation of capillary perfusion and density.

In alternate embodiments, sensing at different wavelengths can be used to implement ratiometric detection to facilitate separation of contributions from light scattering by the tissue and absorption by the blood and to suppress motion artifacts. Sensing employing different wavelengths may utilize common or differing structures for the delivery of photonic signals to the skin surface, e.g. multiple LEDs utilizing a common fiber optic for delivery of differing photonic signals of differing wavelengths. In addition, the various light sources may be rapidly turned on and off such that signals from one wavelength do not interfere with those of another during the course of a measurement cycle.

In addition, photonic energies responsive to blood components other than those in the visible wavelengths may also be employed. Such energies may include near infrared, mid-range infrared or ultraviolet.

In certain instances, photonic energies may interact with tissue structures or components not directly present within the blood, e.g., melanins within the skin cells themselves that may provide indirect indices of blood volume/vessel arrangement and/or tissue structure associated with a disease state.

To provide the necessary photonic energy, alternate means other than light emitting diodes are readily conceivable. Such alternate sources may include vertical cavity semiconductor lasers, liquid crystals, incandescent bulbs, organic light emitting diodes or halogen lamps. Accordingly, the present invention is not restricted to any one form or type of photonic source. In alternate embodiments, an ambient light may be used with a desired detection wavelength selected using appropriate optical filter in front of the photonic detector.

Figure 6:
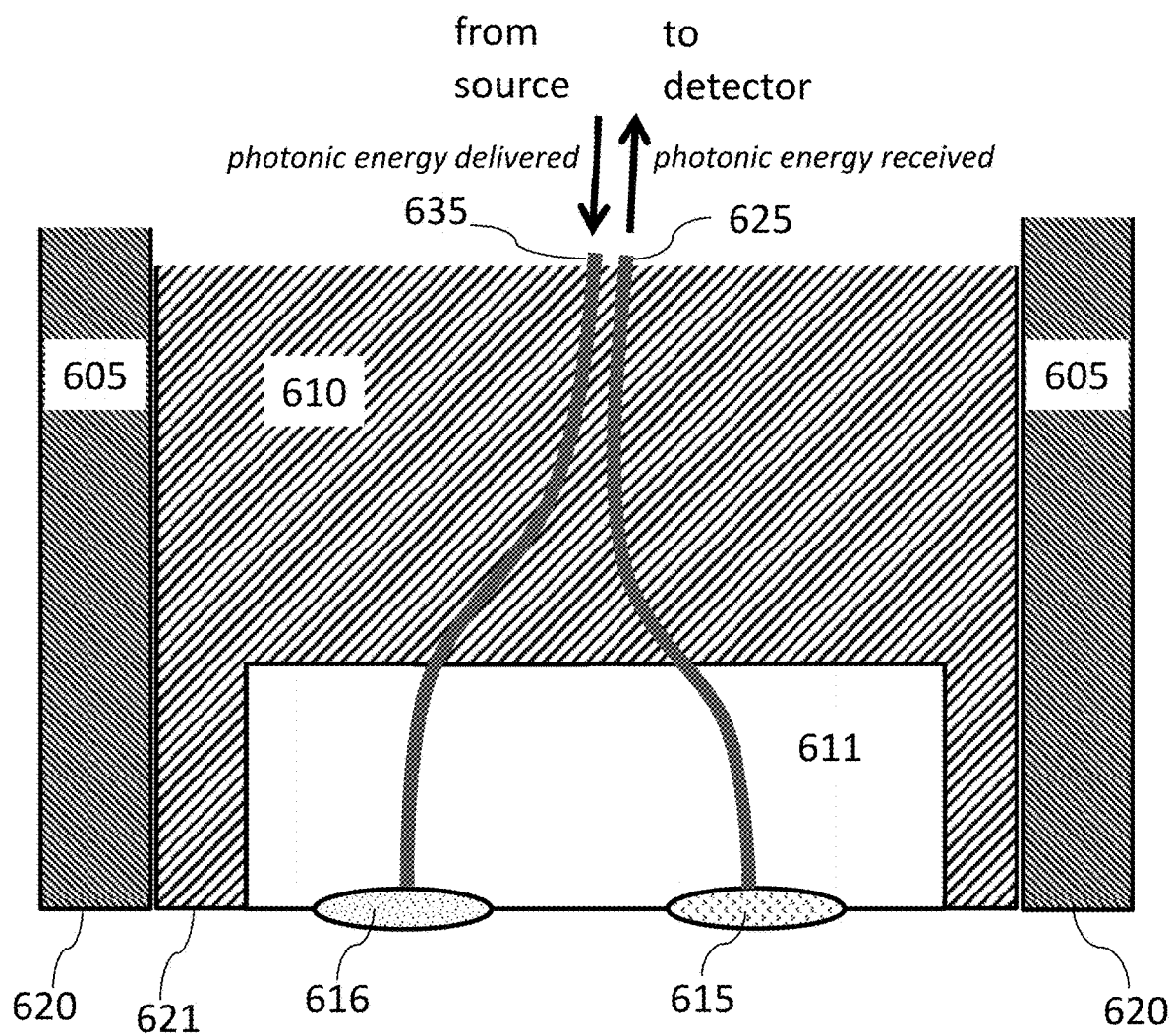
FIG. 6 exemplifies sensor elements of an inner member of a skin perfusion monitoring device.

In exemplary embodiments, photonic energy is delivered to a sensor head located at the end region of an inner member by one or more photonic sources. An example of such an embodiment is shown in FIG. 6, which presents sensor elements of a device provided herein. As shown, the end of inner member 610 contains sensor head 611, which is a structure employed to mount one or more sensing elements within the inner member. Photonic energy is conveyed to lens 616 by fiber optic cable 635. Photonic energy may then be received through lens 615 and conveyed back to a photodetector or other forms of light sensitive structures located elsewhere through fiber optic cable 625. The structure of inner member 610 is enclosed, in part, by outer member 605. Surfaces generally indicated by surfaces 620 and 621 are regions intended to contact skin surface at least in part during operation of the device. It should be understood that within the scope of the present methods and devices disclosed herein, sensor head 611 may not be configured as a separable element distinct from inner member 610.

In this embodiment, lens 616 and 615 may serve to collect and orient photonic energies between the device and the skin surface. Such lenses may be constructed as separate components or be constructed from a larger structure, e.g., by polishing the end of an optic fiber used to transfer photonic energy. In addition, the lens (or other photonic lens or guide) may be configured in or angled in relationship to the surface to optimize signal transmission into body tissue.

Another example may be shown by FIG. 2, wherein photonic energy is delivered to a sensor head 215 by one or more sources located within the electronic component 240 whereby the photonic energy is transmitted to the sensor head via one or more fiber optic cables, represented by connector 235. In other embodiments, the photonic source is located within sensor head 215 and connector 235 serves to supply electrical signals governing the activation of the photonic source. It should be understood that within the scope of the present methods and devices disclosed herein, sensor head 215 may not be configured as a separable element distinct from inner member 210, e.g., a single structure may comprise both functionalities.

In this embodiment, one or more lenses may be employed to collect and orient the emission of photonic energy from the device into the energies between the device and the skin surface. Such lenses may be constructed as separate components or be constructed from a means for conveying the photonic energy to the surface of the sensor head, e.g., by polishing the end a fiber optic. In addition, the angle of the lens, fiber optic (or other photonic lens or guide) may be configured in, or angled in, relationship to the surface 221 to optimize signal transmission into body tissue.

To receive photonic energies after being transmitted into the body tissue, one or more detectors responsive to photonic energy are employed in preferred embodiments of the present methods and devices disclosed herein. Such detectors typically are comprised of one or more semiconductor devices, e.g., photodiodes, wherein the photonic energy is converted to an electrical signal. Other forms of detectors are conceivable, e.g., photomultipliers, and the scope of the methods and devices disclosed herein are not constrained to any one type of photonic energy detector.

In preferred embodiments, one or more photodetectors are located within device electronic circuitry. In such instances, the received photonic energies are transmitted through a fiber optic cable or a fiber optic bundle and connector to the appropriate electronic circuitry and components. Accordingly, in some embodiments, the device may be comprised of a plurality of optical fibers to enable both emission and reception of photonic energy, with various fibers constrained to either emission or reception.

In alternative embodiments, one or more photodetectors may be positioned within the sensor head. In such instances, a connector may serve to convey an electrical signal from the sensor head to electronic circuitry.

As with the emission of photonic energy, in one embodiment, one or more lenses may be employed within the sensor head to orient the received photonic signal to enable subsequent detection and signal analysis. Such lenses may be separate components or a portion of a component, e.g., a polished end of an optical fiber. In addition, the angle of the fiber optic (or other photonic lens or guide) may be configured in relationship to the surface to optimize signal reception from the body tissue.

In preferred embodiments, the sensor head photonic emission source at the surface of the sensor head is positioned in general proximity to where a receiver of the photonic signal is located. In preferred embodiments, an emitter/receiver pair is located in close proximity to each other and effectively flush with the surface of a sensor head, as shown in FIG. 6. The spacing between emitter and receiver is preferably such that the photonic signal propagates in large part through the adjacent skin and tissue and, in one embodiment, is confined primarily to the skin.

In preferred embodiments, the solid elements comprising the components where light is emitted from the sensor head and resultant signals are received, e.g., the lens, are effectively flush with the surface of the sensor head such that an effectively planar surface over the entire surface is achieved.

In alternate embodiments, one or both of the components may be slightly recessed or slightly extruded relative to the surface sensor head. Such arrangements may lessen the likelihood of immediate transfer of photonic signal from emitter to receiver thereby reducing available signal from the body or enhance blood displacement upon application of pressure.

In other alternate embodiments, both signal emitters and receivers are located at the distance from the skin surface providing means to perform measurements of photonic energy reflected from skin; furthermore in the reflectance configuration the use of photonic energy at different wavelengths is desired, thereby providing means for ratiometric determination of time-dependent changes in an effective skin color in response to mechanical or temperature-induced perturbation of skin surface. Skin color changes are one of the indices sensitive to changes in skin capillary density and blood flow.

In general an opaque or material that does not result in significant transference of photonic energies or fluoresce in response to photonic energies employed is desired to comprise the structural aspects of the sensor head, i.e., device components not including those through which photonic signals are intended to travel. Likewise, other aspects of the device, e.g., sections of the outer member and sections of the inner member are generally preferred not to be constructed of materials that transmit photonic energies in the utilized frequencies nor fluoresce in the utilized frequencies, if these sections of these components may be within the photonic path or otherwise interact with the photonic signals.

In other embodiments, the photonic source(s) and photodetector(s) may be located at or in near proximity to a device surface that is intended to contact a skin region for measurement. An illustrative example of one such embodiment is shown in FIG. 7. Panel A of FIG. 7 presents a cross section image of a plurality of photodetectors 703 in near proximity to a photonic source 702. Note that photodetectors 703 and photonic source 702 are at the surface of an inner member 701 and are intended to interact with skin and tissue 705. Not shown are electrical elements, e.g., wires, providing power and signal data between the photodetectors and photonic source and controlling circuitry located elsewhere.

Figure 7B:
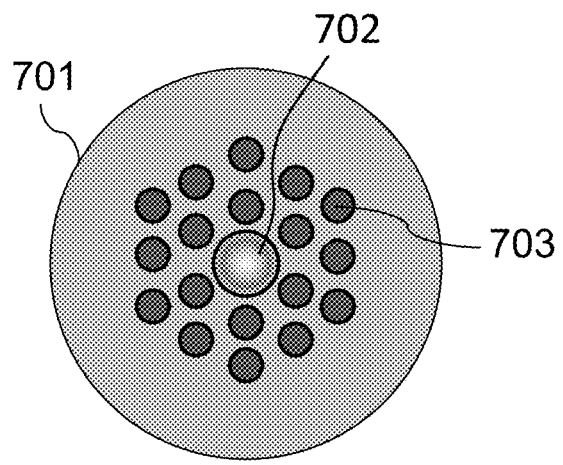

Arrangements of photonic signal emitters and receivers may include other forms than pairs, e.g., a plurality of receivers to a single emitter or the converse. In other instances, varying numbers and arrangements of receivers and emitters may be employed in a pairwise or non-pairwise fashion or organization. Such arrangements may serve to increase the sensitivity of the device and thereby enable a reduced power of photonic energy to be employed, which in turn may further restrict the measured region to the skin vasculature rather than deeper tissues. FIG. 7B illustrates this point by presenting an array of photodetection elements 703 spaced about a single photonic source 702. Alternatively, arrays of emitters and receivers (or sources and detectors) may be employed. These arrays may serve to provide a two dimensional map of a skin region blood flow. In such instances, various spatial combinations of emitters and receivers may be employed sequentially to provide insight into overall blood vessel arrangement, density and depth and enable simultaneous measurement-based comparison of a lesion area and a healthy surrounding tissue. In other embodiments, various types and spacing of emitters and receivers may be employed to facilitate the use of one or more wavelengths of photonic energies, effectively simultaneously, for enabling the examination of overall blood vessel arrangement, density and depth.

Figure 8:
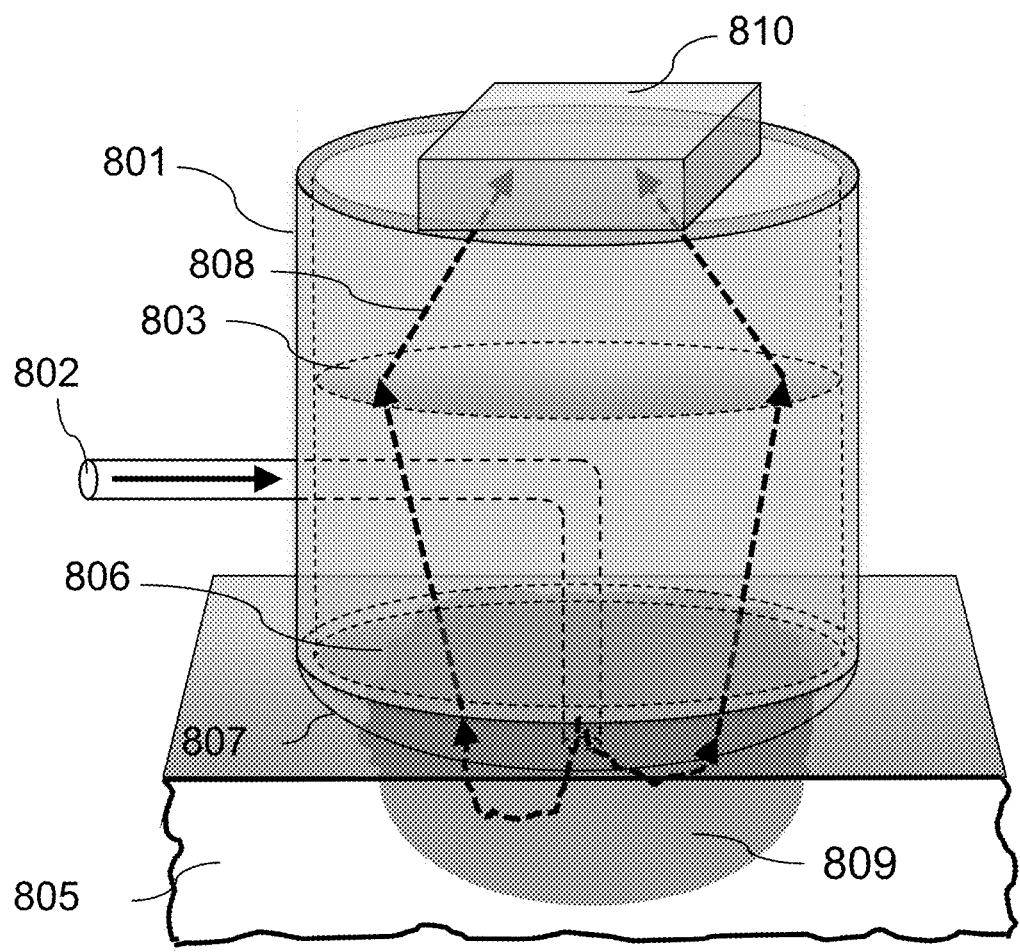
FIG. 8 is illustrative of a sensor of the inner member of a skin perfusion monitoring device, wherein the sensor has an imaging capability.

In yet another embodiment, multi-element photodetectors such as those employed in electronic cameras, e.g., charge coupled devices (CCDs), may be employed as a component of a photonic energy sensor. In such instances, a larger area may be simultaneously measured without the need for multiple fiber optic lines or multiple photodiodes. An example of this form of embodiment is presented in FIG. 8. FIG. 8 presents the portion of an inner member 801 that contacts skin and tissue 805 at inner member surface 807. In this instance, photonic energy is supplied to the skin and tissue region 809 via optic fiber 802 in the direction of the solid arrow. Upon scattering in the tissue of the body region 809, the transmitted light indicated by dashed arrows 808, is collected through the surface of inner member 807 and relayed through lens 803 onto CCD 810. In this example, the composition of structure 806 comprising at least a portion of inner member 801 is effectively transparent, allowing photonic energy 808 to transit from skin region 809 to CCD 810.

The scope of the present methods and devices disclosed herein is not restricted to the use of photonic energies for the determination of amount of blood, blood capillary density, perfusion rate or volume, and blood flow dynamics, either directly or indirectly, in the measured region. Examples of other such energies include, but are not limited to: electromagnetic (radio wave) energy in gigahertz or terahertz frequencies, or ultrasonic energies.

In still other embodiments, sensors that respond to tissue properties, e.g., pressure, motion or temperature, may be employed to help in the determination of blood volume or flow in the measured region. For example, a suitably constructed pressure sensor or transducer may be employed to detect minute movements of the skin associated with pulsatile blood flow through the measured region. Upon the application of pressure resulting in significant loss of blood perfusion through the region, the variation in pressure would be anticipated to diminish significantly.

In yet other embodiments, one or more sensors, e.g., pressure and/or motion/distance, may be employed to aid in the conducting of the measurement cycle. For example, an individual employing the device may manually apply pressure to the inner member in order to displace the blood in the measured skin region. A pressure sensor may then be located on the device in such a location that determination of the pressure of the inner member upon the skin is sensed. Such a sensor may then provide an alert when a predetermined pressure of the inner member on the skin is obtained. Such alerts may be in the form of an indicator light positioned on the device visible to the user or as an audible noise, e.g., a beep. The user, in response to the alert, may then maintain the applied pressure at that level for a desired period of time.

In a related fashion, such a pressure sensor may be part of an automated measurement cycle whereby the automated depression of the inner member on the skin is regulated in part by the use of one or more pressure sensors positioned such that pressure of the inner member against the skin is detected.

In a somewhat similar fashion, a sensor sensing the relative displacement of the inner member relative to the outer member may be employed to aid in the measurement process. That is, the distance traversed by the inner member relative to the outer member once the outer member is positioned against the skin may serve to aid in the operation of the device.

Signals associated with temperature may serve as additional metrics regarding the physiological status of the measured region. For example, it is well known that blood flow to the skin surface may be significantly lessened by cold temperatures due to vasoconstriction. Conversely, blood flow to the skin may be significantly enhanced in those scenarios where the body or regions of the body are attempting to shed heat, i.e. skin vasodilation. In such instances, the use of a temperature sensor, e.g., a thermocouple, positioned on the sensor head to contact the skin may provide data useful in the analysis by enabling corrective terms to be employed. A second temperature sensor positioned elsewhere may also be employed to provide additional useful temperature data, e.g., ambient air temperature, which may be employed in the subsequent data analysis.

In a somewhat different use of temperature, the area to be measured may be intentionally chilled and the recovery of blood perfusion to the region monitored with a device of the present methods and devices disclosed herein. In such instances, the body's vasoconstriction actions serve to limit blood flow to the immediate region. Accordingly, in such embodiments, a device of the present methods and devices disclosed herein may simply monitor the immediate region as the region warms up and blood re-perfuses the region without movement of the inner member. Alternatively, in such embodiments, the inner member and outer member may be constructed as a single unified structure, one in which the inner member is incapable of differential movement with respect to outer member. To chill the skin region, a component such as a Peltier thermoelectric cooler may be incorporated into the device, in particular into one or more areas of the device intended to contact the skin. Alternatively, external cooling means, e.g., an ice cube held against the skin, may be employed.

Similarly, heating the measurement region can also provide additional information disease status in the region of interest. Various means, e.g., heating elements, may be employed to heat the skin region. Similarly, cycling the temperature in conjunction with the measurement can also provide additional information about disease status in the region of interest.

Additional sensors may be included in the device or components of the device, e.g., adhesive tape having one or more sensors incorporated or added, to aid in the operation of the device and/or determination of skin region physiological status. These sensors include but are not limited to: biochemical sensors, e.g., for secreted biomolecules indicative of a disease state, pressure sensors, temperature sensors, pH or ionic sensors, electrical e.g., capacitive sensors, and position or motion sensors, e.g., that aid in a more effective mapping of the boundary of a suspected skin lesion.

In yet other embodiments, video and/or audio sensors may be employed to facilitate device placement and correct alignment on a skin region, e.g., a suspected lesion, or to provide additional information regarding blood and/or disease status. For example, use of a video sensor, e.g., a small camera attachment, may help assist the orientation of the device on the patient or enable the automatic recording of the lesion image in one or more wavelengths of light. Such images, e.g., the overall color or heterogeneity of appearance may assist in the diagnoses of a disease state. Likewise the use of one or more highly sensitive audio pickups or microphones located on or near the device surface in contact with the body may enable additional information regarding blood flow to the general area being measured.

In various embodiments of the present methods and devices disclosed herein, one or more sensors and sensor types may be employed within a device to provide data, enabling the assessment of blood within the measured region.

A number of sensors are conceivable and accordingly, the nature and type of sensors that may be employed within the scope of this disclosure are not limited to those examples and embodiments presented here.

Electronics

In various aspects, in order to enable the functions of the devices provided herein, one or more electronic components are utilized. In exemplary embodiments, a device comprises an inner member and an outer member, wherein the device is configured to measure one or more signals indicative of blood perfusion. In general, these electrical components may govern the automated movement of the inner member relative to the outer member or skin surface, the activation of one or more sensors useful for the determination of blood flow at one or more time points, the analysis and display of results, and any combination thereof.

Figure 9:
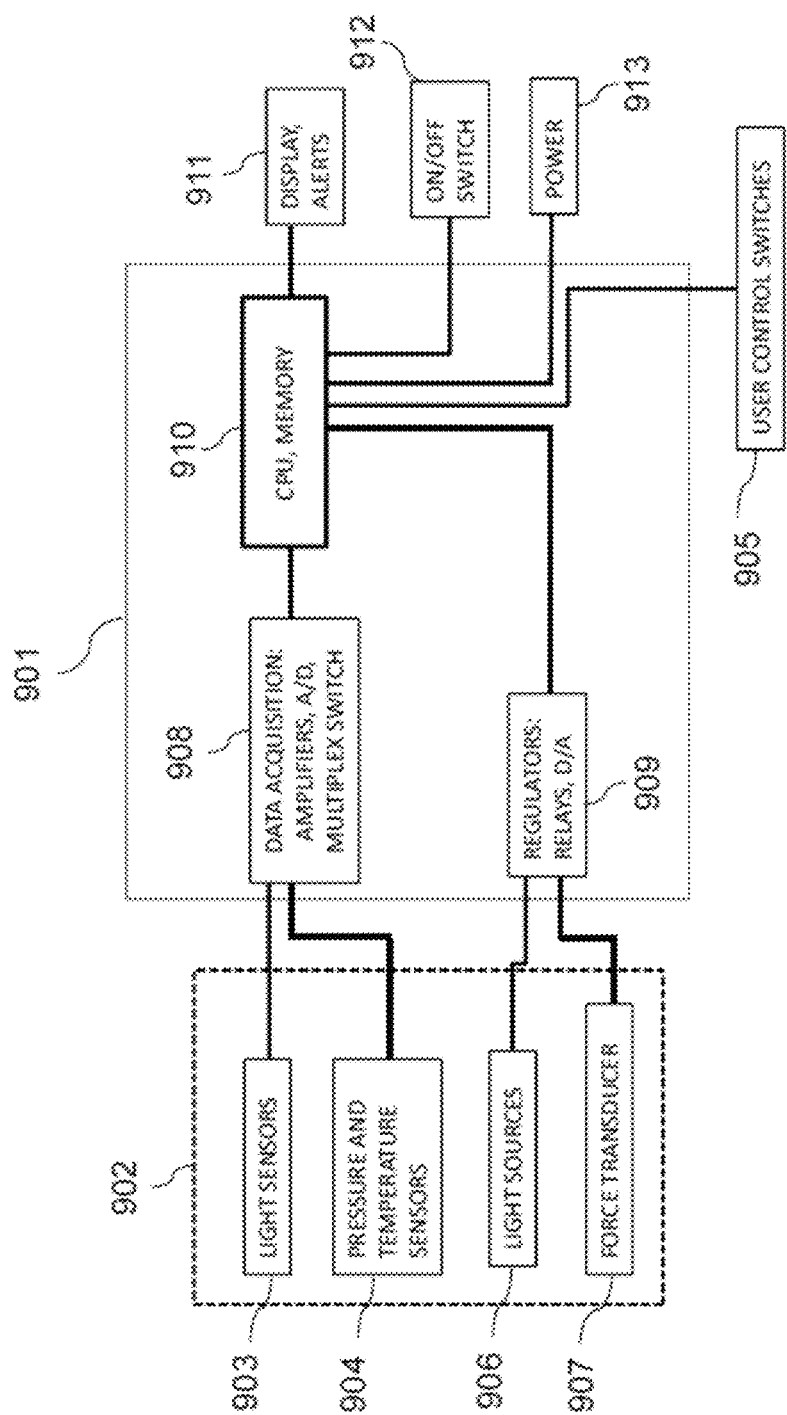
FIG. 9 is an exemplary illustration of electronic circuitry elements enabling operation of a skin perfusion monitoring device.

A representative illustration of electronic circuitry elements enabling such functionalities is presented in FIG. 9. As shown in FIG. 9, contained within electronic circuit 901 is a processing unit 910 having memory. Also present in circuit 901 are other components, e.g., components for digital signal acquisition 908 such as multiplex switch, analog to digital converter, and amplifiers; and components to generate signals 909, e.g., power regulators, relays and digital to analog converters. Such components are typically employed for supplying regulated power to one or more sensors, receiving data from such sensors, as well as the control of electrically operated elements.

Sensors and electrical elements that may be employed by circuitry 901 are generally indicated by the group delineated by box 902 and include, without limitation, photonic sensors 903, pressure and temperature sensors 904, photonic sources 906 and a force transducer 907.

In addition to sensors and electrical elements, circuitry 901 may also have additional inputs and outputs, including, but not limited to, power input 913 (e.g., battery), on/off switch 912 governing overall operation of the device, user controls 905 enabling staged operation of the device, and display or alert 911 for conveying device status and/or measurement data and results via visual and/or audible means.

It will be readily understood that the exact nature and arrangement of circuitry elements will be particular to that embodiment of the device and the example presented here is solely to illustrate the forms and types of circuitry elements enabling the control and operation of a typical device embodiment. Additional components, sensors, actuators, etc. may all involve various permutations of the components and elements presented here and accordingly the scope of the present disclosure is not restricted to that presented in this example.

Likewise, one skilled in the art of electronics will readily appreciate that various elements of the electronic circuitry can be located in various components of the device in order to better enable the overall functionality of the device. For example, certain electronic circuitry elements associated with the control of device operations may be located in the outer member whereas initial signal processing may be located in the inner member. In yet other embodiments, a portion of the data analysis and display may be located in a unit in wired or wireless contact with either the inner or outer member. The exact nature of the placement of electronic elements is therefore governed by the form and requirements of the device embodiment and therefore, the scope of the disclosure is not restricted to any one method or structure for the arrangement of electronic elements.

Data Analysis

In various aspects, data obtained by a device of the present disclosure enables a description of one or more parameters associated with blood flow and/or quantity in the measured region (e.g., skin region). Exemplary parameters include, without limitation, the dimensionality of vasculature, vascularization density, flow resistance, ability of cutaneous blood vessels to vasodilate or vasoconstrict in the measured region, and any combination thereof. Such parameters are useful in the determination of a disease state such as skin cancer when the parameters are compared to normal, non-malignant skin. Furthermore, in various embodiments, it is a desired feature of the present methods and devices disclosed herein that the data obtained by a device of the present disclosure enables a description of the dimensionality and/or quantity of capillary blood vessels in the measured skin region through the measurement of blood capillary perfusion and other related parameters. Such indices are useful in the determination of a disease state, such as cancerous or precancerous states, e.g., a melanoma, as compared to normal, non-malignant skin. That is, it is well known that skin cancers often have a denser capillary network or larger dimensioned vasculature relative to those present in non-cancerous skin or common nevi. For example it has been shown that mean vascular counts in cutaneous malignant melanoma are up to ~324% higher than in common acquired nevi. Moreover a gradual rise in vascularity with tumor progression was observed offering a basis for early detection and for monitoring efficacy of treatment.

Accordingly, assessment of the rate and amplitude by which blood reperfuses a skin region may serve as useful tool in discriminating between a cancerous, atypical and non-cancerous state.

Induction of angiogenesis generally provides a supply of nutrients and oxygen for malignant tissue growth, invasion, and metastasis. In order for a tumor cell to survive, it cannot be more than a few hundred micrometers from the nearest blood vessel. Blood vessel structural abnormalities have been shown to reveal underlying disease very early during the onset of disease; for example, after arrival of only 60 to 80 of tumor cells to an in vivo host tissue it starts to exhibit atypical changes in vasculature and that these changes extend beyond tumor margins. Skin cancers have a denser capillary network or larger dimensioned vasculature relative to those present in non-cancerous skin or common nevi.

For example, mean vascular counts (MVC) in cutaneous malignant melanoma are up to ~324% higher than in common acquired nevi and ~500% higher than in normal skin. Similar increases in MVC may occur in BCC and SCC tumors. Moreover a gradual rise in vascularity with tumor progression offers a basis for early detection, for monitoring efficacy of treatment and prognostic value. Neovascularization in melanoma correlates with poor prognosis, mortality, and elevated rate of relapse. Measurements of passive blood perfusion using high-resolution laser Doppler perfusion imaging exhibit significantly elevated blood flow in primary melanoma tumors as compared to dysplastic melanocytic nevi (2.2×) and normal skin (3.6×); increase blood flow occurs in BCC tumors. Thus, one useful parameter that may be determined within the scope of the present disclosure is a relatively higher amount of blood being present in a suspect region, e.g., the tumor as compared to adjacent normal skin. Therefore, blood volume represents a target parameter that can potentially be used for diagnostic purpose at one or multiple time-points.

Blood flow rate in a tumor is proportional to (a) pressure difference between arterial and venous side and (b) inversely proportional to viscous and geometric resistance of a vascular network. Pressures on the arterial side of tumor and normal tissue are equal, however pressures in more dominant venular vessels of the tumor are significantly lower than in the normal tissue. Moreover many sold tumors have highly elevated interstitial fluid pressure (IFP) which is attributed to leaky capillaries, increased resistance to interstitial fluid flow, and impaired lymphatic drainage. IFP in combination with lower venular pressure has been implicated in being responsible for the vessel collapse, the flow stasis and reversal in tumor vasculature.

Vascular resistance to blood flow in cutaneous cancers is higher by one to two orders of magnitude than in surrounding normal tissues; this increase is due to various factors such as changes in diameter of blood vessels, disorder in the geometry of the vascular network and increased tortuosity of the vessels. Tumor tissues are known to develop vascular networks with major geometrical abnormalities such as heterogeneous vessel distribution, a lack of vessel hierarchy, increased intervessel distances, arterial to venous shunts, excessive branching, and blind vascular ends. Geometrical flow resistance of tumors is nonlinear function to applied pressure. The flow resistance is significantly higher at lower perfusion pressure and then asymptotically decreases to a constant value at higher pressures; such non-linear flow dependence in tumors is in contrast to a constant flow resistance of normal tissues and has been attributed to viscoelasticity of tumor vessels and to cellular pressure exerted by the surrounding tumor cells. Thus, relative changes in a blood flow rate and overall temporal dynamics of blood flow through tumor vasculature as compared to normal vasculature may represent second set of kinetic parameters that can be used for diagnostic purpose.

Another aspect of microcirculation relevant to this project is pressure-induced vasodilation (PIV). Locally applied mechanical pressure induces localized cutaneous vasodilation in the human skin. In contrast newly developed tumor vessels typically lack smooth muscle cells and are less likely to respond to physical or chemical stimuli; i.e. their ability to actively vasodilate is impaired. Accordingly, impaired PIV represents additional parameter that may be exploited for diagnostic purposes.

Additional blood flow parameters or characteristics may forthcoming that also aid in distinguishing between normal skin and underlying tissue and a disease state, e.g., cancer. Accordingly, the scope of parameters that may be determined using the method and devices of the present methods and devices disclosed herein are not limited to those examples presented here.

Figure 10:
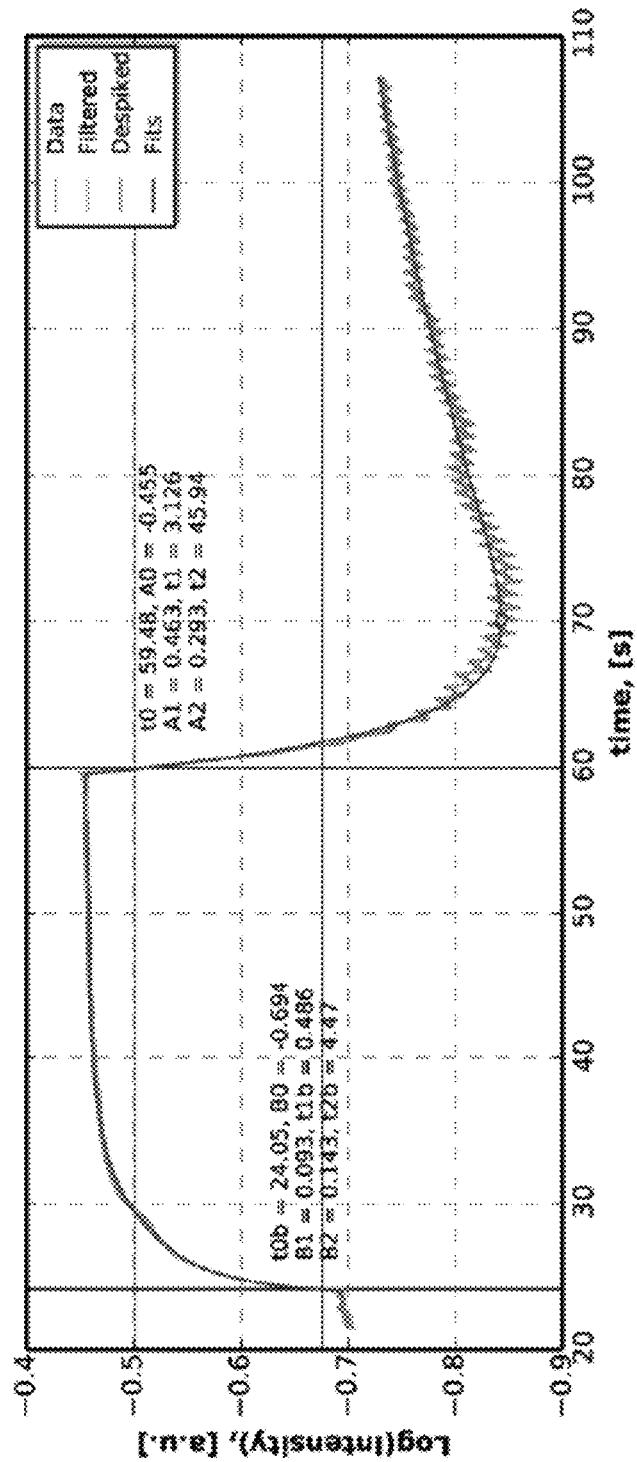
FIG. 10 exemplifies representative data obtained using a skin perfusion monitoring device as described herein.

An example of representative data obtained using a device of the present methods and devices disclosed herein and derivation of measured parameters from this data is presented in FIG. 10, taken from a normal (non-disease) skin region. As shown, the data curve representing the log intensity of received (transmitted) photonic energy remains relatively flat (non-rising) until approximately 25 seconds. At this time, pressure is applied and the signal rises due to the loss of absorbing chromophores, e.g., blood, from the measured region. Note that instead of signal rising, a decrease can also be observed if the shape of the inner member in contact with skin is flat or concave due to pooling of the blood in the compressed area.

The dynamics of pressure-induced signal increase exhibits fast and slow rise components. One component may be attributed in part to the removal from the immediate region of chromophores present within the blood. These chromophores absorb, at least in part, the applied photonic energy. When the chromophores in blood, e.g., hemoglobin, are absent, i.e., removed by the pressure, more of the applied signal is therefore transmitted via scattering through the skin tissue. The other component altered by compression is the scattering path of the photonic signal which is changed due to dimensional changes in the cells and extracellular space and redistribution of interstitial fluid under compression; the present inventors have shown that the contribution of such scattering component is significantly smaller than that caused by blood removal so that the signal is dominated by pressure-induced hemodynamics.

Upon release of pressure, at approximately 60 seconds, the tissue rapidly decompresses (typically within several seconds), resulting in an influx of blood back into the local vessels. This influx results in a decrease over time of measured signal to levels approximating the initial, pre-compression state. The relaxation of the signal back to the approximate baseline level is characterized by fast and slow decay components. In one possible interpretation the decompression may be thought of as having two major components, one being the relatively immediate expansion of tissue back to original dimension and the second being the relatively slower refilling of the local blood vessels from which the blood was removed. In another possible interpretation the faster and slower components are dues to refill of larger and smaller vessels, respectively.

In this instance, the absolute level of the signal returns to a level lower than the initial state then over time returns to the initial baseline level, e.g., at approximately 110 seconds. As shown in FIG. 10, this reduction below baseline levels is attributed to pressure induced vasodilation (PIV) which over time, diminishes back to initial conditions.

In various instances, one or more attributes of a signal obtained from a measured region during the course of these manipulations may not precisely match the pattern of the signal described here. For example, the baseline itself may drift or change over a period of time. In such instances, these variations may be accounted for mathematically to enable direct comparison to other signals obtained elsewhere. Alternatively, these variations may in themselves prove of diagnostic value and therefore be employed in the analysis for determination of a disease state being present. The scope of the present methods and devices disclosed herein therefore is not restricted to data or measured values having the precise shape, forms and magnitudes of those data examples presented here.

A variety of mathematical tools and approaches may be employed for the analysis of these data. For example, the data obtained following the cessation of pressure may be treated as the sum of one, two or more exponential curves. Utilizing standard mathematical approaches, e.g., least squares fitting, to arrive at mathematical solutions for the parameters of the curves, values such as estimated lifetimes ($t_1$, $t_2$) and signal amplitudes (A, B) may be determined that describe the rate of signal decrease in each curve and amplitudes of decay and rise components such as those shown in FIG. 10. In this instance, the rate of relaxation of the signal back to its lowest point so determined is represented by the term $t_1$.

The absolute magnitude of the signal rise from baseline may be defined by parameters $A_0$-$B_0$ and may be considered to approximately represent the absolute volume of chromophores (blood) displaced from the measured region.

Alternative analysis includes using the maximum entropy method to obtain a distribution of lifetimes (and corresponding decay rates) without any assumptions about the functional form of such distribution. Such lifetime distribution provides a more realistic model for the blood flow analysis in tissues containing a number of blood vessels with different diameters and densities.

In yet another general analysis approach the amplitudes, temporal gradients and temporal shapes of the hemodynamic profiles for skin cancer diagnosis can be quantified.

Other parameters, e.g., maximal signal amplitude, may be determined using additional mathematical techniques such as signal averaging, etc. In related embodiments, other body parameters such as heart rate may be determined through analysis of the signal data, e.g., analysis of pulsatile repetitive patterns within data set following reperfusion.

The analysis of temporal relationships and correlations between signals from multiple detectors sampling photonic energies at different distances from the light source and at different wavelengths can be used to determine both the lateral and vertical spatial velocities of capillary refill which provides another parameter to selectively characterize flow of blood preferentially along parallel or vertical directions to skin surface.

Once determined, one or more of these parameters may be utilized to assess the likelihood of a disease state in the immediate skin region. Such determinations may be accomplished in a variety of ways. For example, measurements from a suspected skin area may be compared to those of an adjacent area presumed to be healthy or in a non-disease state. If the measures differ by more than a specified amount, then a disease state or probability of a disease state being present may be assigned.

Alternatively, parameters derived from measurements of a suspected skin area may be compared against tabulated values or algorithms obtained through clinical studies examining multiple individuals and lesions. Such comparisons might be performed either electronically or manually. If the values differ by more than a specified amount, then a disease state or probability of a disease state such as melanoma within the measured skin area may be then arrived at.

Alternatively, the present methods and devices disclosed herein can be used for monitoring of suspected area of skin for treatment efficacy assessment.

The scope of the present methods and devices disclosed herein is not constrained to any one form or method of data analysis or determination of probability of disease state.

Figure 11A:
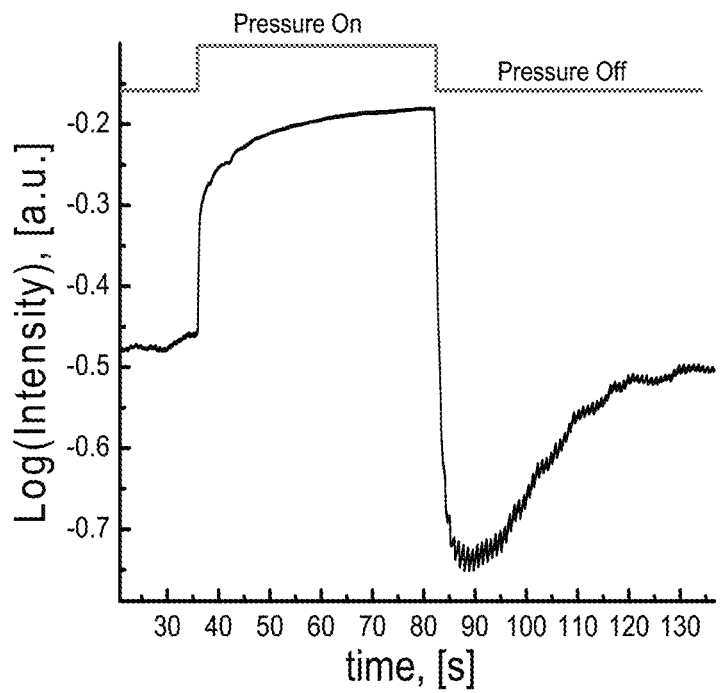
FIGS. 11A-C exemplify representative data from (FIG. 11A) normal skin.
Figure 11B:
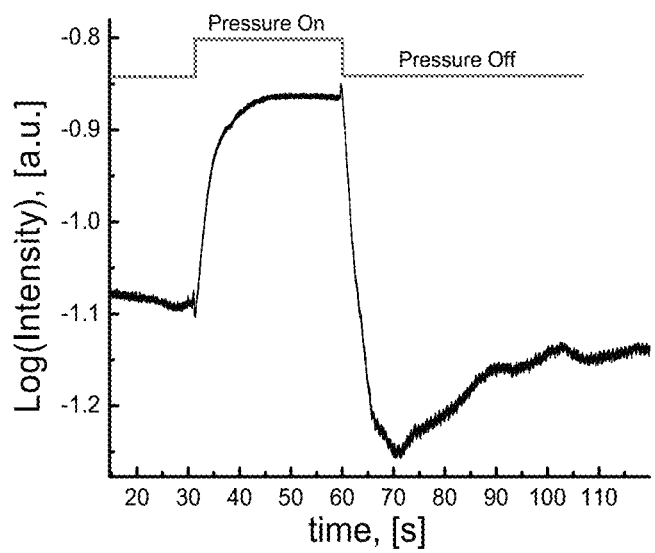
Figure 11C:
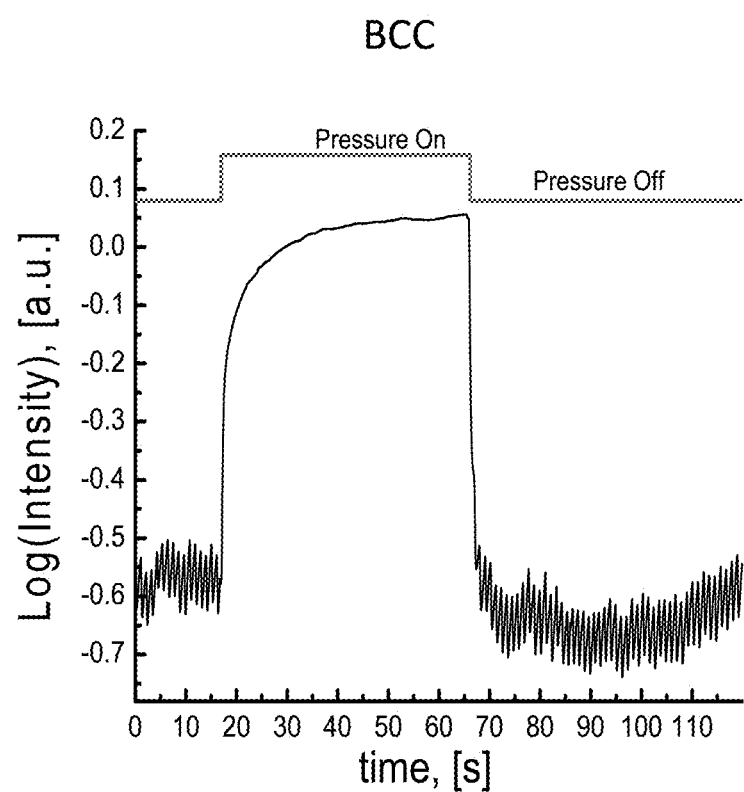
Figure 12A:
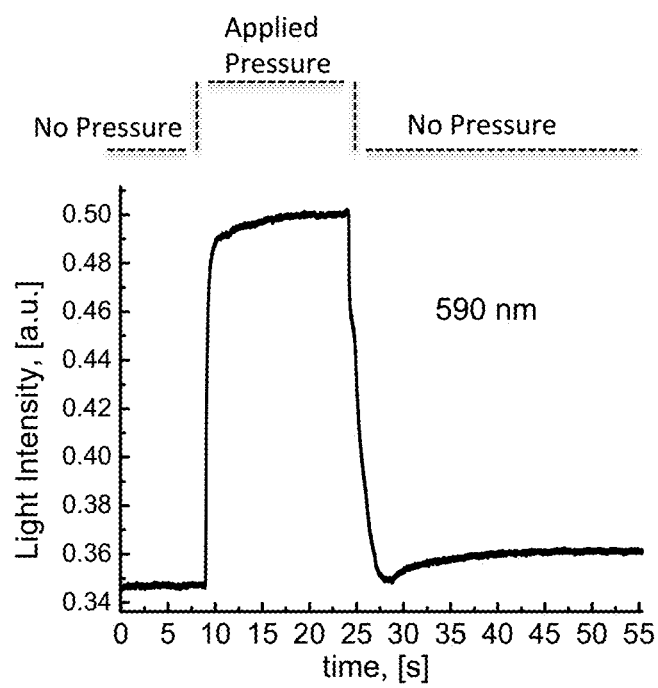
FIGS. 12A-D are illustrative of pressure-induced hemodynamics with wavelength of light emitted from a skin perfusion monitoring device.
Figure 12B:
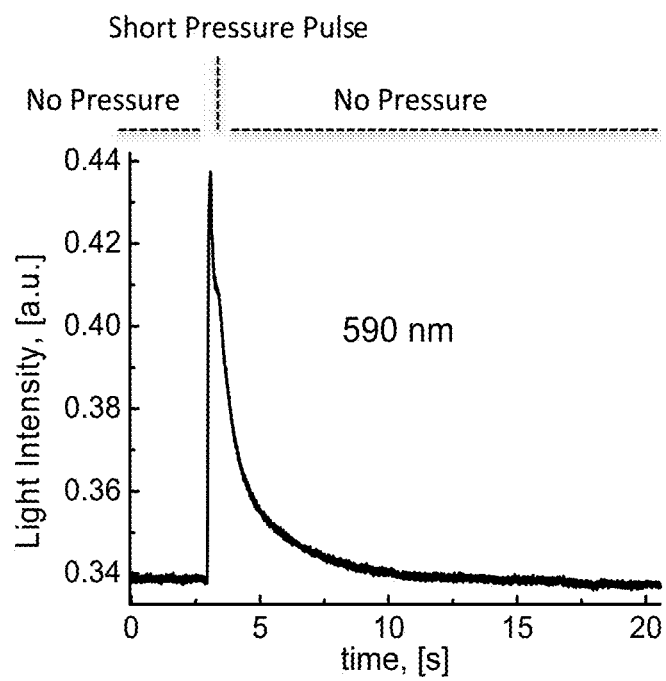
Figure 12C:
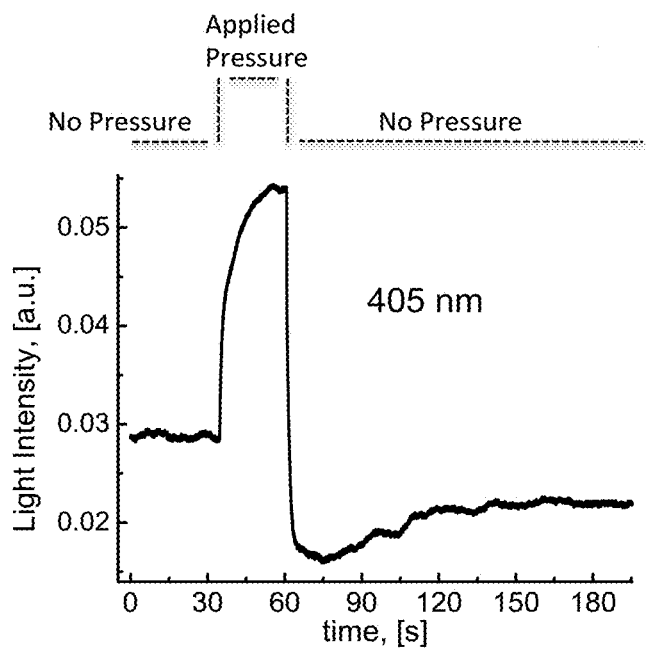
Figure 12D:
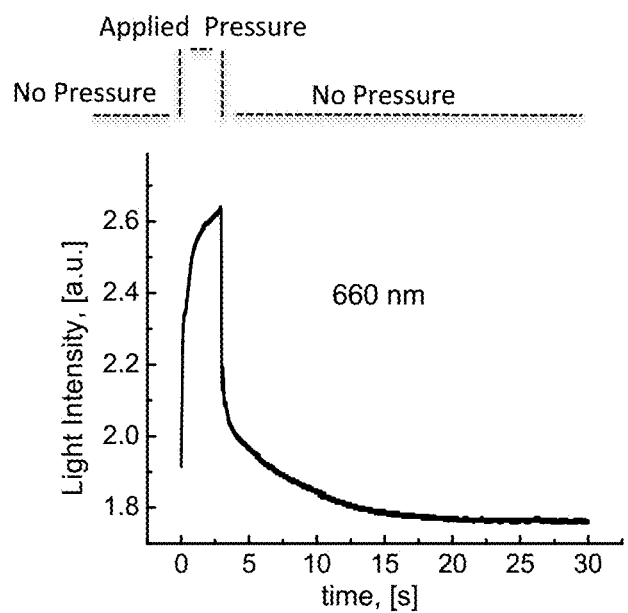

FIG. 11 presents data from normal skin (FIG. 11A); a benign nevus, i.e., a mole, (FIG. 11B); and a confirmed basal cell carcinoma, BCC, (FIG. 11C). All three present the same general profile. That is, the signals generally exhibit a steady baseline value in the absence of pressure. However, upon the application of pressure, the signals rise and asymptotically approach a maximum plateau in each instance. Then, upon the cessation of pressure, the signal rapidly decreases back to approximately baseline levels. Closer inspection reveals differences between these graphs, however. For instance, it may be noted that in Panel C, the BCC has minimal or no reduction of signal below that of baseline values, an observation attributable to an inhibited or reduced PIV response in the cancerous tissue. Through use of various forms of mathematical analyses, the present methods and devices disclosed herein enables determination of disease states in skin regions.

In an alternate example, consider a scenario using a device as disclosed herein whereby blood is forced out of a skin region, then allowed to perfuse back in, all the while being monitored using an photonic energy, e.g., 405 nm, 590 nm or 660 nm light source where excitation and detection areas on the skin are within 1 mm distance.

FIGS. 12 A-D illustrates that signal dynamics are dependent on the wavelength of light used. For example FIG. 12C shows that, in general, both signal rise and recovery dynamics is slower at shorter interrogation wavelength (405 nm) as compared to dynamics at 590 nm (FIG. 12A, FIG. 12B) or 660 nm (FIG. 12D). This may be attributable in part to significantly reduced light penetration depths at shorter wavelengths, thereby light at these wavelengths probing dynamics mainly in the capillaries near skin surface. It is a desired feature of the methods and devices disclosed herein to use different wavelengths of light to probe and enable characterization of vascularity at different depths in the tissue.

In alternate embodiments, energies other than photonic energy may be employed, e.g., ultrasound radiation may be used to monitor cutaneous blood dynamics. In one possible embodiment both ultrasound emitter and ultrasound detector are co-located in the inner member; and a time-gated detection system is used to selectively detect cutaneous hemodynamic. In alternate embodiment the light modulated at the ultrasound frequency is absorbed by the blood leading to the emission of ultrasonic radiation at said frequency which is detected by an ultrasound detector co-located next to the light source.

Data in FIG. 12 also suggest that signal dynamic is dependent on the duration and the magnitude of applied pressure leading in some cases to inversion of signal change after removal of applied pressure, most apparent at 405 nm (FIG. 12C); such feature is related, in general, to interplay between active physiological response of the tissue, light scattering and absorption providing novel information for tissue characterization or diagnostic of atypical response. For example the decrease of the signal below the initial baseline following the release of the pressure (FIG. 12C) is due in part to pressure-induced vasodilation which is a characteristic response of a normal cutaneous tissue; the PIV may be partly or completely inhibited in malignant tissues as shown in FIG. 11C, providing an additional parameter that can be used to increase diagnostic power of the method and device.

Figure 13:
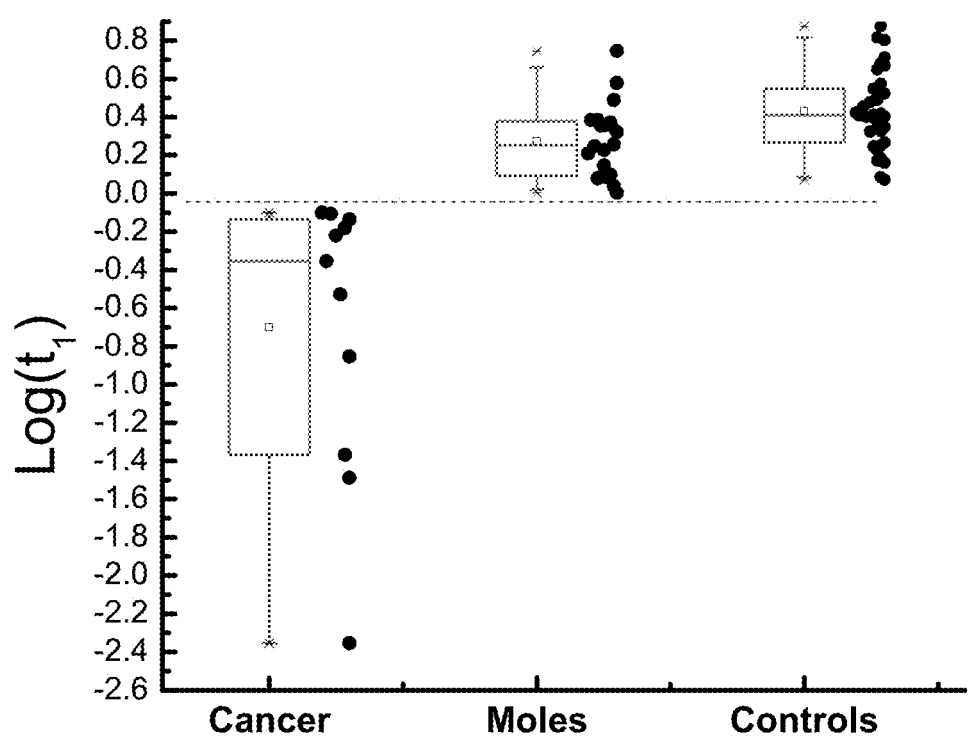
FIG. 13 provides results from a clinical study on human subjects illustrating differences in one pressure-induced hemodynamic parameter (a refill time constant) in normal tissue, benign moles and skin cancers measured using a skin perfusion monitoring device.

Results of one such form of analyses utilizing data obtained with a device of the present methods and devices disclosed herein employing pressure to dynamically affect skin blood flow are presented in FIG. 13. As shown, values of a parameter associated with the rate of signal reduction following pressure cessation, t1, are similar, i.e., not significantly different, between those of moles (or benign nevi) and those normal skin (controls). Values obtained from cancerous skin tissue (as subsequently determined through histological analysis), differed however from those of either moles or normal skin. These data clearly demonstrate the ability of measurements obtained with a device of the present methods and devices disclosed herein to usefully distinguish between various skin health states.

Figure 14:
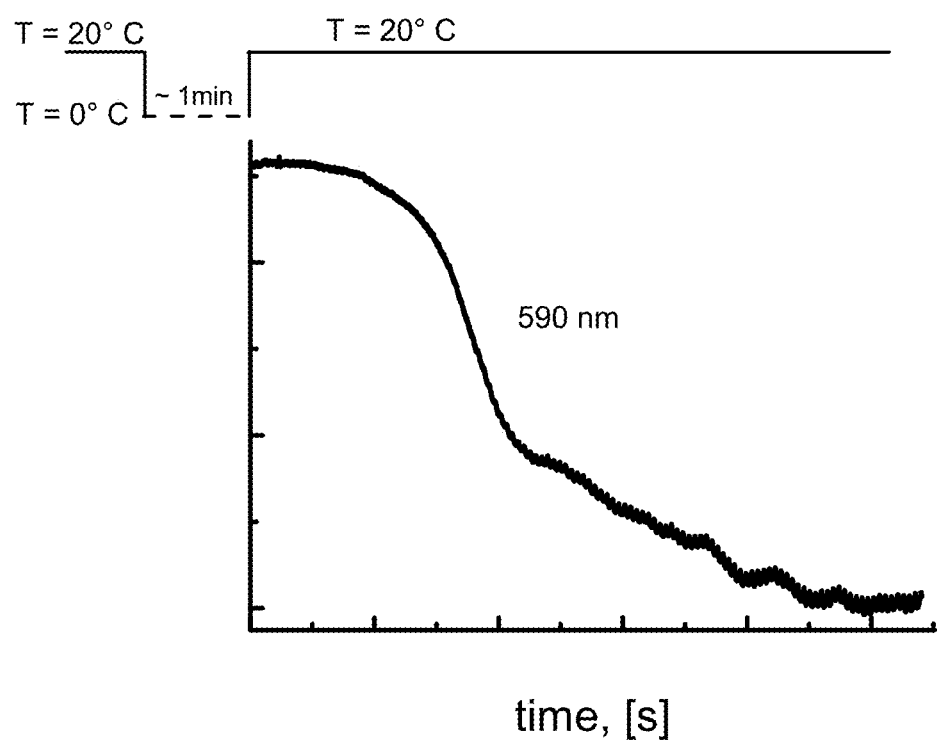
FIG. 14 is illustrative of exemplary data obtained using a skin perfusion monitoring device under temperature perturbation.

As an alternate form of manipulation of blood flow within a skin region, temperature may be employed. An example of the influence of temperature on skin blood flow is shown in FIG. 14. In this example, the skin region was chilled by placement of an ice cube on the surface prior to measurements. Upon removal of the ice, the skin region was then measured using a device of the present methods and devices disclosed herein without the use of applied pressure. As shown, the signal decreased over time. This decrease is attributable to the skin region warming up and a cessation or relaxation of cold-induced vasoconstriction. One can readily conceive of device embodiments wherein the use of temperature is employed, with or without the use of applied pressure, to manipulate vascular status and thereby obtain measurements useful for the determination of disease states.

In yet other forms of the methods and devices disclosed herein, pressure may be employed to enhance the pooling or retention of blood within a measured region. Such retention or engorgement of blood may be through a variety of means, e.g., the employment of a negative local pressure, higher pressure on a perimeter of a measured area or the concave shape of the inner member as described above. Upon cessation of this applied pressure (negative or positive), blood flowing through one or more capillary networks may then be measured to arrive at one or more parameters descriptive of such networks. In form, a pooling of blood may result in a reversal of signals observed, e.g., upon application of pressure in this instance, the baseline signal would decrease further due to the increased concentration of absorbing chromophores, e.g., hemoglobin in blood, in the measured region. Upon release, blood volume would decrease through surrounding capillary networks and thereby provide useful information regarding capillary volume and blood flow dynamics. Accordingly, the present methods and devices disclosed herein also includes those forms of the methods and devices disclosed herein wherein the application of the device results in an accumulation of blood in the measured region and is not restricted to forms of the methods and devices disclosed herein causing the removal of blood from a measured region.

Data analysis using measurements may be performed within the electronics of the device itself, or may be performed in part or in whole upon transference of some or all of the data or mathematical transforms of the data or parameters to one or more data processing units, e.g., laptop computers, internet-based data storage and computing centers, etc. In certain embodiments, measurements can be taken one or more times, e.g., a baseline measurement and one or more measurements.

Such transference of data may be accomplished by wireless, e.g., Bluetooth or WiFi, communication means using appropriately configured electronics within the electronics section 140. Alternatively, wired means, e.g., direct electrical connection between the device and an external device such as a laptop computer, may be employed.

The device itself may present data, parameters, analysis, findings and/or operational status using displays or indicators. Accordingly, displays may utilize alphanumeric characters, simple lights, sounds or other means of conveying information to the user of the device.

Overall, the scope of the present methods and devices disclosed herein is not limited to the examples presented herein. Additional forms of the methods and devices disclosed herein are readily conceivable as well as are forms of the methods and devices disclosed herein involving various combinations of the embodiments presented herein and therefore are within the scope of the methods and devices disclosed herein.

EXAMPLES

The application may be better understood by reference to the following non-limiting examples, which are provided as exemplary embodiments of the application. The following examples are presented in order to more fully illustrate embodiments and should in no way be construed, however, as limiting the broad scope of the application.

Devices of the methods and devices disclosed herein may be employed for a variety of uses and applications. Such applications include Example 1: Skin Lesion Assessment In this example, a device as disclosed herein may be employed by a clinician to assess a suspect skin lesion, e.g., a mole-like growth, for characteristics associated with a cancerous state.

The clinician would position the end of the device on a suspected skin lesion, e.g., such that the inner member sensor head was located at the area to be examined. The clinician would then activate the device while maintaining the device against the skin surface using the outer member. The operational cycle would then automatically occur resulting in a local depression of the skin followed by relief of the pressure. Measurements would be taken automatically by the device. The measurement would then be repeated on the normal-looking skin in the general area of the body where the lesion is located to obtain reference data.

The data from the measurements would be automatically computed and a score indicative of the probability of a cancerous state being present or possibly occurring in the future would then be displayed on the device.

The clinician could then utilize this information to better guide subsequent actions concerning the patient's health, e.g., recommend removal of the lesion by a surgical procedure.

Example 2: Thermal Response Skin Lesion Assessment

This example is follows Example 1 above, with the exception that after performing the initial exam with the device, the clinician then chills the suspected area of skin by placing a small cube of ice against it for a short period of time, e.g., 1-2 minutes. The clinician then immediately places the device against the area again and monitors the recovery of perfusion due to thermal rise, rather than pressure-related recovery. FIG. 4 shows an example of signal recovery after cooling measured using 590 nm light. Alternatively a sensor with a built-in cooling or heating element can be used to facilitate such measurement.

Example 3: Hand-Held Device for Consumer Use

In this example, a device as disclosed herein may be employed by a consumer to assess a suspect skin lesion, e.g., a mole-like growth, for characteristics associated with a cancerous state.

The consumer would position the end of the device on a suspected skin lesion, e.g., such that the inner member sensor head was located at the area to be examined. The consumer would then activate the device while maintaining the device against the skin surface using the outer member. The operational cycle would then automatically occur resulting in a local depression of the skin followed by relief of the pressure. Measurements would be taken automatically by the device. The measurement would then be repeated on the normal-looking skin in the general area of the body where the lesion is located to obtain reference data.

The data from the measurements would be automatically computed and a score indicative of the probability of a cancerous state being present or possibly occurring in the future would then be displayed on the device.

After performing the initial exam with the device, the consumer then chills the suspected area of skin by placing a small cube of ice against it for a short period of time, e.g., 1-2 minutes. The consumer then immediately places the device against the area again and monitors the recovery of perfusion due to thermal rise, rather than pressure-related recovery. FIG. 4 shows an example of signal recovery after cooling measured using 590 nm light. Alternatively a sensor with a built-in cooling or heating element can be used to facilitate such measurement.

The consumer could then utilize this information to determine if the consumer should contact a clinician for further assessment. The clinician can then better guide subsequent actions concerning the patient's health, e.g., recommend removal of the lesion by a surgical procedure.

Additional applications and uses of the methods and devices disclosed herein are conceivable and therefore the scope of possible applications is not limited to those examples presented above.

REFERENCES

1 Dudewicz, E. J. & Van Der Meulen, E. C. Entropy-Based Tests of Uniformity. Journal of the American Statistical Association 76, 967-974, doi:10.1080/01621459.1981.10477750 (1981).
2 Khan, F., Patterson, D., Belch, J. J., Hirata, K. & Lang, C. C. Relationship between peripheral and coronary function using laser Doppler imaging and transthoracic echocardiography. Clin Sci (Lond) 115, 295-300, doi:10.1042/CS20070431 (2008).
3 Cracowski, J. L., Minson, C. T., Salvat-Melis, M. & Halliwill, J. R. Methodological issues in the assessment of skin microvascular endothelial function in humans. Trends Pharmacol Sci 27, 503-508, doi:10.1016/j.tips.2006.07.008 (2006).
4 Holowatz, L. A. & Kenney, W. L. Local ascorbate administration augments NO- and non-NO-dependent reflex cutaneous vasodilation in hypertensive humans. Am J Physiol Heart Circ Physiol 293, H1090-1096, doi: 10.1152/ajpheart.00295.2007 (2007).
5 Rousseau, P. et al. Axon-reflex cutaneous vasodilatation is impaired in type 2 diabetic patients receiving chronic low-dose aspirin. Microvasc Res 78, 218-223, doi: 10.1016/j.mvr.2009.06.005 (2009).
6 Struijker-Boudier, H. A. et al. Evaluation of the microcirculation in hypertension and cardiovascular disease. Eur Heart J 28, 2834-2840, doi:10.1093/eurheartj/ehm448 (2007).
7 Turner, J., Belch, J. J. & Khan, F. Current concepts in assessment of microvascular endothelial function using laser Doppler imaging and iontophoresis. Trends in cardiovascular medicine 18, 109-116, doi:10.1016/j.tcm.2008.02.001 (2008).
8 Gokce, N. Clinical assessment of endothelial function: ready for prime time? Circulation. Cardiovascular imaging 4, 348-350, doi:10.1161/CIRCIMAGING.111.966218 (2011).
9 Holowatz, L. A., Thompson-Torgerson, C. S. & Kenney, W. L. The human cutaneous circulation as a model of generalized microvascular function. Journal of applied physiology 105, 370-372, doi:10.1152/japplphysiol.00858.2007 (2008).

10 Holowatz, L. A., Santhanam, L., Webb, A., Berkowitz, D. E. & Kenney, W. L. Oral atorvastatin therapy restores cutaneous microvascular function by decreasing arginase activity in hypercholesterolaemic humans. J Physiol 589, 2093-2103, doi:10.1113/jphysiol.2010.203935 (2011).

11 Khalil, Z., LoGiudice, D., Khodr, B., Maruff, P. & Masters, C. Impaired peripheral endothelial microvascular responsiveness in Alzheimer's disease. Journal of Alzheimer's disease: JAD 11, 25-32 (2007).

12 Ming, Z., Siivola, J., Pietikainen, S., Narhi, M. & Hanninen, O. Postoperative relieve of abnormal vasoregulation in carpal tunnel syndrome. Clinical neurology and neurosurgery 109, 413-417, doi:10.1016/j.clineuro.2007.02.014 (2007).

13 Israel, A. K. et al. Peripheral endothelial dysfunction in patients suffering from acute schizophrenia: a potential marker for cardiovascular morbidity? Schizophr Res 128, 44-50, doi:10.1016/j.schres.2011.02.007 (2011).

14 Hogas, S. M. et al. Methods and potential biomarkers for the evaluation of endothelial dysfunction in chronic kidney disease: a critical approach. Journal of the American Society of Hypertension: JASH 4, 116-127, doi:10.1016/j.jash.2010.03.008 (2010).

15 Sokolnicki, L. A., Roberts, S. K., Wilkins, B. W., Basu, A. & Charkoudian, N. Contribution of nitric oxide to cutaneous microvascular dilation in individuals with type 2 diabetes mellitus. American journal of physiology. Endocrinology and metabolism 292, E314-318, doi: 10.1152/ajpendo.00365.2006 (2007).

16 Rossi, M., Carpi, A., Galata, F., Franzoni, F. & Santoro, G. The investigation of skin blood flowmotion: a new approach to study the microcirculatory impairment in vascular diseases? Biomedicine & pharmacotherapy=Biomedecine & pharmacotherapie 60, 437-442, doi:10.1016/j.biopha.2006.07.012 (2006).

17 Green, D. J. et al. Impaired skin blood flow response to environmental heating in chronic heart failure. Eur Heart J 27, 338-343, doi:10.1093/eurheartj/ehi655 (2006).

18 Roustit, M., Simmons, G. H., Carpentier, P. & Cracowski, J. L. Abnormal digital neurovascular response to local heating in systemic sclerosis. Rheumatology (Oxford) 47, 860-864, doi:10.1093/rheumatology/ken065 (2008).

19 Rossi, M. et al. Skin vasodilator function and vasomotion in patients with morbid obesity: effects of gastric bypass surgery. Obes Surg 21, 87-94, doi:10.1007/s11695-010-0286-9 (2011).

20 Holowatz, L. A., Thompson, C. S. & Kenney, W. L. L-Arginine supplementation or arginase inhibition augments reflex cutaneous vasodilatation in aged human skin. J Physiol 574, 573-581, doi:10.1113/jphysio1.2006.108993 (2006).

21 Thompson-Torgerson, C. S., Holowatz, L. A., Flavahan, N. A. & Kenney, W. L. Rho kinase-mediated local cold-induced cutaneous vasoconstriction is augmented in aged human skin. Am J Physiol Heart Circ Physiol 293, H30-36, doi:10.1152/ajpheart.00152.2007 (2007).

22 Trzepizur, W. et al. Microvascular endothelial function in obstructive sleep apnea: Impact of continuous positive airway pressure and mandibular advancement. Sleep medicine 10, 746-752, doi:10.1016/j.sleep.2008.06.013 (2009).

23 Spronk, P. E., Zandstra, D. F. & Ince, C. Bench-to-bedside review: sepsis is a disease of the microcirculation. Crit Care 8, 462-468, doi:10.1186/cc2894 (2004).

24 Alba-Alejandre, I., Hiedl, S. & Genzel-Boroviczeny, O. Microcirculatory changes in term newborns with suspected infection: an observational prospective study. International journal of pediatrics 2013, 768784, doi: 10.1155/2013/768784 (2013).

25 Takkin, L., Sample, R., Moore, P. & P., G. Prediction of Wound Healing Outcome using Skin Perfusion Pressure & Transcutaneous Oximetry. Wounds 21 (2009).

26 Shapiro, J. & Nouvong, A. in Topics in the Prevention, Treatment and Complications of Type 2 Diabetes (ed Mark Zimering) (InTech, 2011).

27 Carmeliet, P. & Jain, R. K. Angiogenesis in cancer and other diseases. Nature 407, 249-257, doi:10.1038/35025220 (2000).

28 Nishida, N., Yano, H., Nishida, T., Kamura, T. & Kojiro, M. Angiogenesis in cancer. Vascular health and risk management 2, 213-219 (2006).

29 Folkman, J. Angiogenesis in cancer, vascular, rheumatoid and other disease. Nat Med 1, 27-31 (1995).

30 Emmett, M. S., Dewing, D. & Pritchard-Jones, R. O. Angiogenesis and melanoma—from basic science to clinical trials. American journal of cancer research 1, 852-868 (2011).

31 Li, C. Y. et al. Initial stages of tumor cell-induced angiogenesis: evaluation via skin window chambers in rodent models. Journal of the National Cancer Institute 92, 143-147 (2000).

32 Velasco, P. & Lange-Asschenfeldt, B. Dermatological aspects of angiogenesis. The British journal of dermatology 147, 841-852 (2002).

33 Chin, C. W., Foss, A. J., Stevens, A. & Lowe, J. Differences in the vascular patterns of basal and squamous cell skin carcinomas explain their differences in clinical behaviour. The Journal of pathology 200, 308-313, doi:10.1002/path.1363 (2003).

34 Srivastava, A., Laidler, P., Davies, R. P., Horgan, K. & Hughes, L. E. The prognostic significance of tumor vascularity in intermediate-thickness (0.76-4.0 mm thick) skin melanoma. A quantitative histologic study. Am J Pathol 133, 419-423 (1988).

35 Kashani-Sabet, M., Sagebiel, R. W., Ferreira, C. M., Nosrati, M. & Miller, J. R., 3rd. Tumor vascularity in the prognostic assessment of primary cutaneous melanoma. J Clin Oncol 20, 1826-1831 (2002).

36 Toth-Jakatics, R., Jimi, S., Takebayashi, S. & Kawamoto, N. Cutaneous malignant melanoma: correlation between neovascularization and peritumor accumulation of mast cells overexpressing vascular endothelial growth factor. Human pathology 31, 955-960 (2000).

37 Barnhill, R. L., Fandrey, K., Levy, M. A., Mihm, M. C., Jr. & Hyman, B. Angiogenesis and tumor progression of melanoma. Quantification of vascularity in melanocytic nevi and cutaneous malignant melanoma. Lab Invest 67, 331-337 (1992).

38 Weidner, N. Intratumor microvessel density as a prognostic factor in cancer. Am J Pathol 147, 9-19 (1995).

39 Straume, O., Salvesen, H. B. & Akslen, L. A. Angiogenesis is prognostically important in vertical growth phase melanomas. Int J Oncol 15, 595-599 (1999).

40 Ria, R. et al. Angiogenesis and progression in human melanoma. Dermatology research and practice 2010, 185687, doi:10.1155/2010/185687 (2010).

41 Stucker, M. et al. High-resolution laser Doppler perfusion imaging aids in differentiating between benign and malignant melanocytic skin tumours. Acta dermato-venereologica 82, 25-29 (2002).

42 Jain, R. K. Determinants of tumor blood flow: a review. Cancer Res 48, 2641-2658 (1988).

43 Simonsen, T. G., Gaustad, J. V., Leinaas, M. N. & Rofstad, E. K. High interstitial fluid pressure is associated with tumor-line specific vascular abnormalities in human melanoma xenografts. PLoS One 7, e40006, doi:10.1371/journal.pone.0040006 (2012).
44 Lunt, S. J., Fyles, A., Hill, R. P. & Milosevic, M. Interstitial fluid pressure in tumors: therapeutic barrier and biomarker of angiogenesis. Future oncology 4, 793-802, doi:10.2217/14796694.4.6.793 (2008).
45 Heldin, C. H., Rubin, K., Pietras, K. & Ostman, A. High interstitial fluid pressure—an obstacle in cancer therapy. Nat Rev Cancer 4, 806-813, doi:10.1038/nrc1456 (2004).
46 Less, J. R., Posner, M. C., Skalak, T. C., Wolmark, N. & Jain, R. K. Geometric resistance and microvascular network architecture of human colorectal carcinoma. Microcirculation 4, 25-33 (1997).
47 Sevick, E. M. & Jain, R. K. Geometric resistance to blood flow in solid tumors perfused ex vivo: effects of tumor size and perfusion pressure. Cancer Res 49, 3506-3512 (1989).
48 Gaustad, J. V., Simonsen, T. G., Brurberg, K. G., Huuse, E. M. & Rofstad, E. K. Blood supply in melanoma xenografts is governed by the morphology of the supplying arteries. Neoplasia 11, 277-285 (2009).
49 Lyng, H., Skretting, A. & Rofstad, E. K. Blood flow in six human melanoma xenograft lines with different growth characteristics. Cancer Res 52, 584-592 (1992).
50 Sensky, P. L., Prise, V. E., Tozer, G. M., Shaffi, K. M. & Hirst, D. G. Resistance to flow through tissue-isolated transplanted rat tumours located in two different sites. British journal of cancer 67, 1337-1341 (1993).
51 Baish, J. W. & Jain, R. K. Fractals and cancer. Cancer Res 60, 3683-3688 (2000).
52 Gessner, R. C., Aylward, S. R. & Dayton, P. A. Mapping microvasculature with acoustic angiography yields quantifiable differences between healthy and tumor-bearing tissue volumes in a rodent model. Radiology 264, 733-740, doi:10.1148/radiol.12112000 (2012).
53 Garry, A. et al. Cellular mechanisms underlying cutaneous pressure-induced vasodilation: in vivo involvement of potassium channels. Am J Physiol Heart Circ Physiol 289, H174-180, doi:10.1152/ajpheart.01020.2004 (2005).
54 Abraham, P., Fromy, B., Merzeau, S., Jardel, A. & Saumet, J. L. Dynamics of local pressure-induced cutaneous vasodilation in the human hand. Microvasc Res 61, 122-129, doi:10.1006/mvre.2000.2290 (2001).
55 Fromy, B. et al. Early decrease of skin blood flow in response to locally applied pressure in diabetic subjects. Diabetes 51, 1214-1217 (2002).
56 Livesey, A. K. & Brochon, J. C. Analyzing the distribution of decay constants in pulse-fluorimetry using the maximum entropy method. Biophys J 52, 693-706 (1987).
57 Jacques, S. L. Optical properties of biological tissues: a review. Physics in medicine and biology 58, R37-61, doi:10.1088/0031-9155/58/11/R37 (2013).

What is claimed is:

1. A device for measuring blood microcirculation, the device comprising:
an inner member comprising a rounded, outwardly protruding surface capable of moving towards and contacting a skin region and providing an external force to the skin region;
an outer member, wherein the inner member is configured to move relative to the outer member, allowing for application of variable pressure to the skin region;
a slide button, a spring, a track, and a pin disposed within the track, wherein movement of the slide button in a first direction causes the pin to move down the track, thereby causing the spring to move the inner member in an outward motion to depress the inner member against the skin region to provide the external force to the skin region, wherein the external force is sufficient in pressure and duration to alter blood perfusion in the skin region;
the inner member comprising a sensor comprising a photonic excitation source and a photonic detector, wherein the sensor is capable of measuring a blood flow parameter prior to, during, and/or after application of the external force to the skin region.

2. The device according to claim 1, wherein the outer member comprises at least one surface region configured to be in substantial contact with a region proximal to the skin region contacted by the inner member during movement of the inner member.

3. The device according to claim 1, wherein the rounded, outwardly protruding of the inner member comprises a convex, cylindrical, parabolic, or spherical surface for exerting pressure on the skin region.

4. The device according to claim 1, wherein the device is configured to analyze the measured blood flow parameter and determine a presence of a disease state in a subject.

5. The device according to claim 4, wherein the disease state is hypercholesterolemia, Alzheimer disease, carpal tunnel syndrome, schizophrenia, hypertension, renal disease, type 2 diabetes, peripheral vascular disease, atherosclerotic coronary artery disease, heart failure, systemic sclerosis, obesity, primary aging, sleep apnea, neonatal & adult sepsis, wound healing, or a combination thereof.

6. The device according to claim 1, wherein the sensor is localized within the rounded, outwardly protruding surface of the inner member.

7. The device according to claim 1, wherein the sensor detects transmitted light from the skin region.

8. The device according to claim 1, further comprising a second spring, wherein the second spring biases the inner member away from the skin region.

9. The device according to claim 1, wherein movement of the slide button in a second direction causes the second spring to move the inner member away from the skin region returning the inner member to an initial state to remove the external force from the skin region.

10. The device according to claim 1, wherein the external force is about 1 kPa to about 100 kPa.

11. The device according to claim 1, wherein the external force is about 4 kPa to about 50 kPa.

12. The device according to claim 1, wherein the photonic detector comprises an array of photodetection elements spaced about the photonic excitation source.

13. The device according to claim 12, wherein the photonic excitation source comprises an array of photonic emitters.

14. The device according to claim 1, wherein the outer member comprises a rod-like structure having a length of about 7 centimeters to about 15 centimeters.

15. The device according to claim 14, wherein the outer member comprises a diameter of about 1 centimeter to about 4 centimeters.

16. The device according to claim 1, further comprising a disposable component comprising an adhesive and an opening to allow the inner member to traverse through the outer member and thereby contact the skin region, wherein the adhesive adheres the device to the skin region, wherein the disposable component is separable from the outer member.

* * * * *